(12) United States Patent
Lavon et al.

(10) Patent No.: US 9,333,120 B2
(45) Date of Patent: May 10, 2016

(54) DISPOSABLE ABSORBENT ARTICLE HAVING BREATHABLE SIDE FLAPS

(71) Applicant: The Procter & Gamble Company, Cincinnati, OH (US)

(72) Inventors: Gary Dean Lavon, Liberty Township, OH (US); Kevin Michael Smith, Cincinnati, OH (US); Michael Patrick Hayden, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/590,044

(22) Filed: Jan. 6, 2015

(65) Prior Publication Data

US 2015/0112291 A1   Apr. 23, 2015

Related U.S. Application Data

(63) Continuation of application No. 11/133,818, filed on May 20, 2005, now abandoned.

(51) Int. Cl.
*A61F 13/15* (2006.01)
*A61F 13/20* (2006.01)
*A61F 13/49* (2006.01)
(Continued)

(52) U.S. Cl.
CPC ....... *A61F 13/49017* (2013.01); *A61F 13/4942* (2013.01); *A61F 13/49413* (2013.01); *A61F 13/53713* (2013.01); *A61F 13/4946* (2013.01); *A61F 2013/15121* (2013.01); *A61F 2013/4512* (2013.01); *A61F 2013/4948* (2013.01);
(Continued)

(58) Field of Classification Search
USPC .................................... 604/385.01, 367, 378
See application file for complete search history.

(56) References Cited

U.S. PATENT DOCUMENTS

| 1,733,997 A | 10/1929 | Marr |
| 1,734,499 A | 11/1929 | Marinsky |

(Continued)

FOREIGN PATENT DOCUMENTS

| CN | 1371671 | 2/2001 |
| DE | 10204937 | 8/2003 |

(Continued)

OTHER PUBLICATIONS

International Search Report, mailed Sep. 18, 2006, 3 pages.

(Continued)

*Primary Examiner* — Michele M Kidwell
(74) *Attorney, Agent, or Firm* — Andrew J. Hagerty

(57) ABSTRACT

A simple disposable absorbent article including a chassis and an absorbent assembly. The chassis includes a water-impermeable sheet folded laterally inward at both of its side edges to form opposing side flaps. Each side flap is attached to the interior surface of the chassis adjacent to its end edges. Each side flap has a longitudinally extending elastic gathering member attached adjacent to its proximal edge. The absorbent assembly is smaller in width and in length than the chassis. The side edges and end edges of the absorbent assembly may be disposed proximally relative to the respective side edges and end edges of the chassis. The absorbent assembly includes an absorbent core that may contain superabsorbent particles, which may be contained inside pockets. The chassis may be extensible. The absorbent assembly may be in a cruciform pattern to the chassis to allow portions of the chassis to extend laterally.

11 Claims, 14 Drawing Sheets

(51) Int. Cl.
*A61F 13/494* (2006.01)
*A61F 13/537* (2006.01)
*A61F 13/58* (2006.01)
*A61F 13/45* (2006.01)
*A61F 13/53* (2006.01)

(52) U.S. Cl.
CPC .............. *A61F2013/530007* (2013.01); *A61F 2013/530481* (2013.01); *A61F 2013/587* (2013.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,009,063 A | 2/1977 | Wood |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievit et al. |
| 4,551,191 A | 11/1985 | Kock et al. |
| 4,573,986 A | 3/1986 | Minetola et al. |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,609,518 A | 9/1986 | Curro et al. |
| 4,610,678 A | 9/1986 | Weisman et al. |
| 4,629,643 A | 12/1986 | Curro et al. |
| 4,636,207 A | 1/1987 | Buell |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,680,030 A | 7/1987 | Coates et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,785,996 A | 11/1988 | Ziecker et al. |
| 4,795,454 A | 1/1989 | Dragoo |
| 4,800,102 A | 1/1989 | Takada |
| 4,802,884 A | 2/1989 | Fröidh et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,861,652 A | 8/1989 | Lippert et al. |
| 4,869,724 A | 9/1989 | Scripps |
| 4,886,697 A | 12/1989 | Perdelwitz, Jr et al. |
| 4,888,231 A | 12/1989 | Angstadt |
| 4,892,528 A | 1/1990 | Suzuki et al. |
| 4,892,535 A | 1/1990 | Bjornberg et al. |
| 4,892,536 A | 1/1990 | DesMarais et al. |

(56) References Cited

U.S. PATENT DOCUMENTS

| | | |
|---|---|---|
| 4,894,060 A | 1/1990 | Nestegard |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,030,314 A | 7/1991 | Lang |
| 5,032,120 A | 7/1991 | Freeland et al. |
| 5,037,416 A | 8/1991 | Allen et al. |
| 5,071,414 A | 12/1991 | Elliott |
| 5,085,654 A | 2/1992 | Buell |
| 5,087,255 A | 2/1992 | Sims |
| 5,092,861 A | 3/1992 | Nomura et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| 5,312,386 A | 5/1994 | Correa et al. |
| 5,331,059 A | 7/1994 | Engelhardt et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,397,316 A | 3/1995 | LaVon et al. |
| 5,397,317 A | 3/1995 | Thomas |
| 5,409,771 A | 4/1995 | Dahmen et al. |
| H1440 H | 5/1995 | New et al. |
| 5,411,497 A | 5/1995 | Tanzer et al. |
| 5,425,725 A | 6/1995 | Tanzer et al. |
| 5,429,630 A | 7/1995 | Beal et al. |
| 5,433,715 A | 7/1995 | Tanzer et al. |
| 5,460,622 A | 10/1995 | Dragoo et al. |
| 5,476,458 A | 12/1995 | Glaug et al. |
| 5,486,167 A | 1/1996 | Dragoo et al. |
| 5,492,751 A * | 2/1996 | Butt, Sr. ............. A61F 13/51401 428/198 |
| 5,494,622 A | 2/1996 | Heath et al. |
| 5,499,978 A | 3/1996 | Buell et al. |
| 5,507,736 A | 4/1996 | Clear et al. |
| 5,509,915 A | 4/1996 | Hanson et al. |
| 5,518,801 A | 5/1996 | Chappell et al. |
| 5,527,300 A | 6/1996 | Sauer |
| 5,531,730 A | 7/1996 | Dreier |
| 5,532,323 A | 7/1996 | Yano et al. |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,622,589 A | 4/1997 | Johnson et al. |
| 5,624,424 A | 4/1997 | Saisaka et al. |
| 5,625,222 A | 4/1997 | Yoneda et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,643,238 A | 7/1997 | Baker |
| 5,643,243 A | 7/1997 | Klemp |
| 5,643,588 A | 7/1997 | Roe et al. |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,303 A * | 10/1997 | Mills .................. A61F 13/4752 604/373 |
| 5,690,627 A | 11/1997 | Clear et al. |
| 5,691,035 A | 11/1997 | Chappell et al. |
| 5,691,036 A | 11/1997 | Lin et al. |
| 5,700,254 A | 12/1997 | McDowall et al. |
| 5,704,928 A * | 1/1998 | Morita ................ A61F 13/4752 604/385.04 |
| 5,714,156 A | 2/1998 | Schmidt et al. |
| 5,723,087 A | 3/1998 | Chappell et al. |
| 5,749,866 A | 5/1998 | Roe et al. |
| 5,752,947 A | 5/1998 | Awolin |
| 5,756,039 A | 5/1998 | Mcfall et al. |
| 5,762,641 A | 6/1998 | Bewick-Sonntag et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,797,894 A | 8/1998 | Cadieux et al. |
| 5,814,035 A | 9/1998 | Gryskiewicz et al. |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,846,232 A | 12/1998 | Serbiak et al. |
| 5,849,816 A | 12/1998 | Suskind et al. |
| 5,851,204 A | 12/1998 | Mizutani |
| 5,865,823 A | 2/1999 | Curro |
| 5,873,868 A | 2/1999 | Nakahata |
| 5,876,391 A | 3/1999 | Roe et al. |
| 5,879,751 A | 3/1999 | Bogdanski |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,931,825 A | 8/1999 | Kuen et al. |
| 5,938,648 A | 8/1999 | LaVon et al. |
| 5,938,650 A | 8/1999 | Baer et al. |

(56) References Cited

U.S. PATENT DOCUMENTS

| | | |
|---|---|---|
| 5,941,862 A | 8/1999 | Haynes et al. |
| 5,944,706 A | 8/1999 | Palumbo et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,083,210 A | 7/2000 | Young et al. |
| 6,090,994 A | 7/2000 | Chen |
| 6,102,892 A | 8/2000 | Putzer et al. |
| 6,103,814 A | 8/2000 | vanDrongelen et al. |
| 6,107,537 A | 8/2000 | Elder et al. |
| 6,110,157 A | 8/2000 | Schmidt |
| 6,117,121 A | 9/2000 | Faulks et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,720 A | 10/2000 | Blenke et al. |
| 6,132,411 A | 10/2000 | Huber et al. |
| 6,139,912 A | 10/2000 | Onuschak et al. |
| 6,143,821 A | 11/2000 | Houben |
| 6,156,424 A | 12/2000 | Taylor |
| 6,165,160 A | 12/2000 | Suzuki et al. |
| 6,174,302 B1 | 1/2001 | Kumasaka |
| 6,177,607 B1 | 1/2001 | Blaney et al. |
| 6,186,996 B1 | 2/2001 | Martin |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,258,996 B1 | 7/2001 | Goldman |
| 6,265,488 B1 | 7/2001 | Fujino et al. |
| 6,290,686 B1 | 9/2001 | Tanzer et al. |
| 6,319,239 B1 | 11/2001 | Daniels et al. |
| 6,322,552 B1 | 11/2001 | Blenke et al. |
| 6,325,787 B1 | 12/2001 | Roe et al. |
| 6,330,735 B1 | 12/2001 | Hahn et al. |
| 6,334,858 B1 | 1/2002 | Rönnberg et al. |
| 6,350,332 B1 | 2/2002 | Thomas et al. |
| 6,368,687 B1 | 4/2002 | Joseph et al. |
| 6,376,034 B1 | 4/2002 | Brander |
| 6,383,431 B1 | 5/2002 | Dobrin et al. |
| 6,402,729 B1 | 6/2002 | Boberg et al. |
| 6,402,731 B1 | 6/2002 | Suprise et al. |
| 6,403,857 B1 | 6/2002 | Gross et al. |
| 6,413,249 B1 | 7/2002 | Turi et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,048 B1 | 7/2002 | Suzuki et al. |
| 6,429,350 B1 | 8/2002 | Tanzer et al. |
| 6,432,098 B1 | 8/2002 | Kline et al. |
| 6,432,099 B2 | 8/2002 | Rönnberg |
| 6,443,933 B1 | 9/2002 | Suzuki et al. |
| 6,458,877 B1 | 10/2002 | Ahmed et al. |
| 6,461,342 B2 | 10/2002 | Tanji et al. |
| 6,461,343 B1 | 10/2002 | Schaefer et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,979 B1 | 1/2003 | Funk et al. |
| 6,520,947 B1 | 2/2003 | Tilly et al. |
| 6,524,294 B1 | 2/2003 | Hilston et al. |
| 6,529,860 B1 | 3/2003 | Strumolo et al. |
| 6,534,149 B1 | 3/2003 | Daley et al. |
| 6,559,239 B1 | 5/2003 | Riegel et al. |
| 6,569,137 B2 | 5/2003 | Suzuki et al. |
| 6,573,422 B1 | 6/2003 | Rosenfeld et al. |
| 6,585,713 B1 | 7/2003 | LeMahieu et al. |
| 6,592,562 B2 * | 7/2003 | Menard ............... A61F 13/4752 604/385.04 |
| 6,605,070 B2 | 8/2003 | Ludwig et al. |
| 6,610,900 B1 | 8/2003 | Tanzer |
| 6,632,504 B1 | 10/2003 | Gillespie et al. |
| 6,645,569 B1 | 11/2003 | Cramer et al. |
| 6,646,180 B1 * | 11/2003 | Chmielewski .... A61F 13/15658 428/220 |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,657,015 B1 | 12/2003 | Riegel et al. |
| 6,682,515 B1 | 1/2004 | Mizutani et al. |
| 6,689,115 B1 | 2/2004 | Popp et al. |
| 6,706,129 B2 | 3/2004 | Ando et al. |
| 6,716,441 B1 | 4/2004 | Osborne et al. |
| 6,726,792 B1 | 4/2004 | Johnson et al. |
| 6,730,387 B2 | 5/2004 | Rezai et al. |
| 6,802,834 B2 | 10/2004 | Melius et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,832,905 B2 | 12/2004 | Delzer et al. |
| 6,863,933 B2 | 3/2005 | Cramer et al. |
| 6,863,960 B2 | 3/2005 | Curro et al. |
| 6,878,433 B2 | 4/2005 | Curro et al. |
| 6,880,211 B2 | 4/2005 | Jackson et al. |
| 6,923,797 B2 | 8/2005 | Shinohara et al. |
| 6,923,926 B2 | 8/2005 | Walter et al. |
| 6,946,585 B2 | 9/2005 | Brown |
| 6,962,578 B1 | 11/2005 | LaVon |
| 6,972,010 B2 | 12/2005 | Pesce et al. |
| 6,972,011 B2 | 12/2005 | Maeda et al. |
| 6,982,052 B2 | 1/2006 | Daniels et al. |
| 7,014,632 B2 | 3/2006 | Takino et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,108,916 B2 | 9/2006 | Ehrnsperger et al. |
| 7,112,621 B2 | 9/2006 | Rohrbaugh et al. |
| 7,160,281 B2 | 1/2007 | Leminh et al. |
| 7,163,528 B2 | 1/2007 | Christon et al. |
| 7,241,280 B2 | 7/2007 | Christen et al. |
| 7,270,651 B2 | 9/2007 | Adams et al. |
| 7,285,178 B2 | 10/2007 | Mischler et al. |
| 7,306,582 B2 | 12/2007 | Adams et al. |
| 7,311,696 B2 | 12/2007 | Christen et al. |
| 7,537,832 B2 | 5/2009 | Carlucci et al. |
| 7,598,428 B2 | 10/2009 | Gustavsson et al. |
| 7,736,351 B2 | 6/2010 | Nigam et al. |
| 7,737,324 B2 | 6/2010 | LaVon et al. |
| 7,744,576 B2 | 6/2010 | Busam et al. |
| 7,750,203 B2 | 7/2010 | Becket et al. |
| 7,767,878 B2 | 8/2010 | Suzuki |
| 7,838,722 B2 | 11/2010 | Blessing et al. |
| 7,931,636 B2 | 4/2011 | LaVon et al. |
| 8,167,862 B2 | 5/2012 | Digiacomantonio et al. |
| 8,187,239 B2 | 5/2012 | LaVon |
| 8,258,367 B2 | 9/2012 | Lawson et al. |
| 8,333,749 B2 * | 12/2012 | Tsang ............... A61F 13/15756 604/385.04 |
| 8,734,417 B2 | 5/2014 | LaVon et al. |
| 2002/0007169 A1 | 1/2002 | Graef et al. |
| 2002/0016122 A1 | 2/2002 | Curro et al. |
| 2002/0045881 A1 | 4/2002 | Kusibojoska et al. |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0072471 A1 | 6/2002 | Ikeuchi et al. |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |

(56) References Cited

U.S. PATENT DOCUMENTS

| | | |
|---|---|---|
| 2002/0192366 A1 | 12/2002 | Cramer et al. |
| 2002/0197695 A1 | 12/2002 | Glucksmann et al. |
| 2003/0088223 A1 | 5/2003 | Vogt et al. |
| 2003/0105190 A1 | 6/2003 | Diehl et al. |
| 2003/0109839 A1 | 6/2003 | Costea et al. |
| 2003/0114811 A1 | 6/2003 | Christen et al. |
| 2003/0114818 A1 | 6/2003 | Benecke et al. |
| 2003/0115969 A1 | 6/2003 | Koyano et al. |
| 2003/0120249 A1 | 6/2003 | Wulz et al. |
| 2003/0135176 A1 | 7/2003 | Delzer et al. |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0233082 A1 | 12/2003 | Kline et al. |
| 2003/0236512 A1 | 12/2003 | Baker |
| 2004/0022998 A1 | 2/2004 | Miyamoto et al. |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0170813 A1 | 9/2004 | Digiacomantonio et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2005/0004548 A1 | 1/2005 | Otsubo et al. |
| 2005/0008839 A1 | 1/2005 | Cramer et al. |
| 2005/0038401 A1 | 2/2005 | Suzuki et al. |
| 2005/0085784 A1 | 4/2005 | LeMinh et al. |
| 2005/0101929 A1 | 5/2005 | Waksmundzki et al. |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0288645 A1 | 12/2005 | LaVon |
| 2005/0288646 A1 | 12/2005 | LaVon |
| 2006/0024433 A1 | 2/2006 | Blessing et al. |
| 2006/0069367 A1 | 3/2006 | Waksmundzki et al. |
| 2006/0155057 A1 | 7/2006 | Hermeling et al. |
| 2006/0167215 A1 | 7/2006 | Hermeling et al. |
| 2006/0177647 A1 | 8/2006 | Schmidt et al. |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | LaVon et al. |
| 2006/0271010 A1 | 11/2006 | LaVon |
| 2007/0043191 A1 | 2/2007 | Hermeling et al. |
| 2007/0043330 A1 | 2/2007 | Lankhof et al. |
| 2007/0049897 A1 | 3/2007 | LaVon et al. |
| 2007/0088308 A1 | 4/2007 | Ehrnsperger et al. |
| 2007/0093767 A1 | 4/2007 | Carlucci et al. |
| 2007/0118087 A1 | 5/2007 | Flohr et al. |
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0191798 A1 | 8/2007 | Glaug et al. |
| 2007/0219521 A1 | 9/2007 | Hird et al. |
| 2007/0244455 A1 | 10/2007 | Hansson et al. |
| 2008/0027402 A1 | 1/2008 | Schmidt et al. |
| 2008/0091159 A1 | 4/2008 | Carlucci et al. |
| 2008/0132864 A1 | 6/2008 | Lawson et al. |
| 2008/0312617 A1 | 12/2008 | Hundorf et al. |
| 2008/0312622 A1 | 12/2008 | Hundorf et al. |
| 2009/0192035 A1 | 7/2009 | Stueven et al. |
| 2009/0258994 A1 | 10/2009 | Stueven et al. |
| 2009/0318884 A1 | 12/2009 | Meyer et al. |
| 2010/0051166 A1 | 3/2010 | Hundorf et al. |
| 2010/0068520 A1 | 3/2010 | Stueven |
| 2010/0115237 A1 | 5/2010 | Brewer et al. |
| 2010/0241096 A1 | 9/2010 | LaVon et al. |
| 2011/0112498 A1 | 5/2011 | Nhan et al. |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0165776 A1 | 6/2012 | McGregor et al. |
| 2012/0296301 A1 | 11/2012 | Lawson et al. |
| 2012/0312491 A1 | 12/2012 | Jackels et al. |
| 2012/0316523 A1 | 12/2012 | Hippe et al. |
| 2013/0218115 A1 | 8/2013 | Katsuragawa et al. |
| 2014/0005623 A1 | 1/2014 | Wirtz et al. |

FOREIGN PATENT DOCUMENTS

| | | |
|---|---|---|
| EP | 0149880 | 7/1985 |
| EP | 203289 | 12/1986 |
| EP | 0206208 | 12/1986 |
| EP | 0403832 | 12/1990 |
| EP | 0640330 | 3/1995 |
| EP | 0689817 | 3/1996 |
| EP | 0394274 | 7/1996 |
| EP | 0761194 A2 | 3/1997 |
| EP | 0737055 | 8/1998 |
| EP | 0875224 | 11/1998 |
| EP | 0893115 | 1/1999 |
| EP | 0724418 | 3/1999 |
| EP | 0725613 | 3/1999 |
| EP | 0725616 | 3/1999 |
| EP | 0916327 | 5/1999 |
| EP | 0951890 | 10/1999 |
| EP | 0778762 | 4/2000 |
| EP | 1059072 | 12/2000 |
| EP | 1088537 | 4/2001 |
| EP | 0796068 | 5/2001 |
| EP | 752892 | 7/2001 |
| EP | 1116479 | 7/2001 |
| EP | 0790839 | 8/2001 |
| EP | 0793469 | 6/2002 |
| EP | 1224922 | 7/2002 |
| EP | 1253231 | 10/2002 |
| EP | 0737056 | 1/2003 |
| EP | 1447066 | 8/2004 |
| EP | 1447067 | 8/2004 |
| EP | 1621167 | 2/2006 |
| EP | 1403419 | 5/2006 |
| EP | 1447066 | 10/2008 |
| EP | 1621165 | 4/2010 |
| EP | 2532329 | 12/2012 |
| EP | 2532332 | 12/2012 |
| EP | 2679210 | 1/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1307441 | 2/1973 |
| GB | 1513055 | 6/1978 |
| GB | 2101468 | 1/1983 |
| GB | 2262873 | 7/1993 |
| JP | 2107250 | 4/1990 |
| JP | 04122256 | 4/1992 |
| JP | 04341368 | 11/1992 |
| JP | 06191505 | 7/1994 |
| JP | 06269475 | 9/1994 |
| JP | 07124193 | 5/1995 |
| JP | 08215629 | 8/1996 |
| JP | 200146435 | 9/1999 |
| JP | 11318980 | 11/1999 |
| JP | 11320742 | 11/1999 |
| JP | 2001277394 | 10/2001 |
| JP | 2001321397 | 11/2001 |
| JP | 2002113800 | 4/2002 |
| JP | 2002178429 | 6/2002 |
| JP | 2002325799 | 11/2002 |
| JP | 2003126140 | 5/2003 |
| JP | 2006513824 T | 4/2006 |
| WO | WO9015830 | 12/1990 |

(56) References Cited

FOREIGN PATENT DOCUMENTS

| | | | | |
|---|---|---|---|---|
| WO | WO9219198 | 11/1992 | | |
| WO | WO9321237 | 10/1993 | | |
| WO | WO9516424 | 12/1993 | | |
| WO | WO9516746 | 6/1995 | | |
| WO | WO9521596 | 8/1995 | | |
| WO | WO9524173 | 9/1995 | | |
| WO | WO9526209 | 10/1995 | | |
| WO | WO9529657 | 11/1995 | | |
| WO | WO9534329 | 12/1995 | | |
| WO | WO9619173 | 6/1996 | | |
| WO | WO9629967 | 10/1996 | | |
| WO | WO9711659 | 4/1997 | | |
| WO | WO9816179 | 4/1998 | | |
| WO | WO9913813 | 3/1999 | | |
| WO | WO9934841 | 7/1999 | | |
| WO | WO0000235 | 1/2000 | | |
| WO | 00/03670 | * | 7/2000 | A61F 13/15 |
| WO | WO0115647 | 3/2001 | | |
| WO | WO0264877 A3 | 1/2003 | | |
| WO | WO03009794 | 2/2003 | | |
| WO | WO03079946 | 10/2003 | | |
| WO | WO03101622 | 12/2003 | | |
| WO | WO2004071539 | 8/2004 | | |
| WO | WO2004/105664 | 12/2004 | | |
| WO | WO2005087164 | 9/2005 | | |
| WO | WO2006062258 | 6/2006 | | |
| WO | WO2007000315 | 1/2007 | | |
| WO | WO2009155265 | 12/2009 | | |
| WO | WO2012052172 | 4/2012 | | |

OTHER PUBLICATIONS

Definition of "undulate", Merriam Webster OnLine.
International Search Report and Written Opinion, PCTUS2006019059, date of issuance Nov. 23, 2007.
All Office Actions, Responses and Claims, U.S. Appl. No. 11/133,818.
All Office Actions, Responses and Claims, U.S. Appl. No. 14/539,134.
All Office Actions, Responses and Claims, U.S. Pat. No. 8,258,367.
All Office Actions, Responses and Claims, U.S. Pat. No. 8,664,468.
All Office Actions, Responses and Claims, U.S. Appl. No. 14/150,859.
All Office Actions, Responses and Claims, U.S. Pat. No. 7,750,203.
All Office Actions, Responses and Claims, U.S. Pat. No. 7,851,667.
All Office Actions, Responses and Claims, U.S. Pat. No. 8,766,031.
All Office Actions, Responses and Claims, U.S. Pat. No. 8,319,005.
All Office Actions, Responses and Claims, U.S. Pat. No. 8,791,318.
All Office Actions, Responses and Claims, U.S. Appl. No. 13/198,235.
All Office Actions, Responses and Claims, U.S. Pat. No. 7,744,713.
All Office Actions, Responses and Claims, U.S. Pat. No. 8,343,296.
All Office Actions, Responses and Claims, U.S. Pat. No. 8,784,594.
All Office Actions, Responses and Claims, U.S. Appl. No. 14/331,277.
All Office Actions, Responses and Claims, U.S. Appl. No. 14/535,419.
All Office Actions, Responses and Claims, U.S. Appl. No. 14/100,059.

* cited by examiner

DISPOSABLE ABSORBENT ARTICLE HAVING BREATHABLE SIDE FLAPS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A disposable absorbent article includes a chassis and an absorbent assembly. The chassis includes a water-impermeable center sheet and laterally opposing water vapor-permeable side sheets attached to the center sheet adjacent to its side edges. Laterally opposing portions of the chassis are folded laterally inward and attached to the interior surface of the chassis adjacent to its end edges to form breathable side flaps. Each side flap has a longitudinally extending elastic gathering member attached adjacent to its proximal edge. The absorbent assembly is smaller in width and in length than the chassis. The side edges and end edges of the absorbent assembly may be disposed proximally relative to the respective side edges and end edges of the chassis. The absorbent assembly includes an absorbent core. The absorbent core may contain superabsorbent particles and these particles may be contained inside pockets. The chassis center sheet may be laterally extensible and may include an extensible formed web material. The absorbent assembly may be attached in a cruciform pattern to the chassis to allow portions of the chassis to extend laterally.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In FIG. 1, the interior portion of the diaper 20 that faces inwardly toward the wearer and contacts the wearer is shown facing the viewer.

In FIG. 10, the interior portion of the diaper 20 that faces inwardly toward the wearer and contacts the wearer is shown facing the viewer.

In FIG. 21, the exterior portion of the diaper 20 that faces outwardly away from the wearer is shown facing the viewer.

In FIG. 22, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.

DETAILED DESCRIPTION OF THE INVENTION

Figure 1:
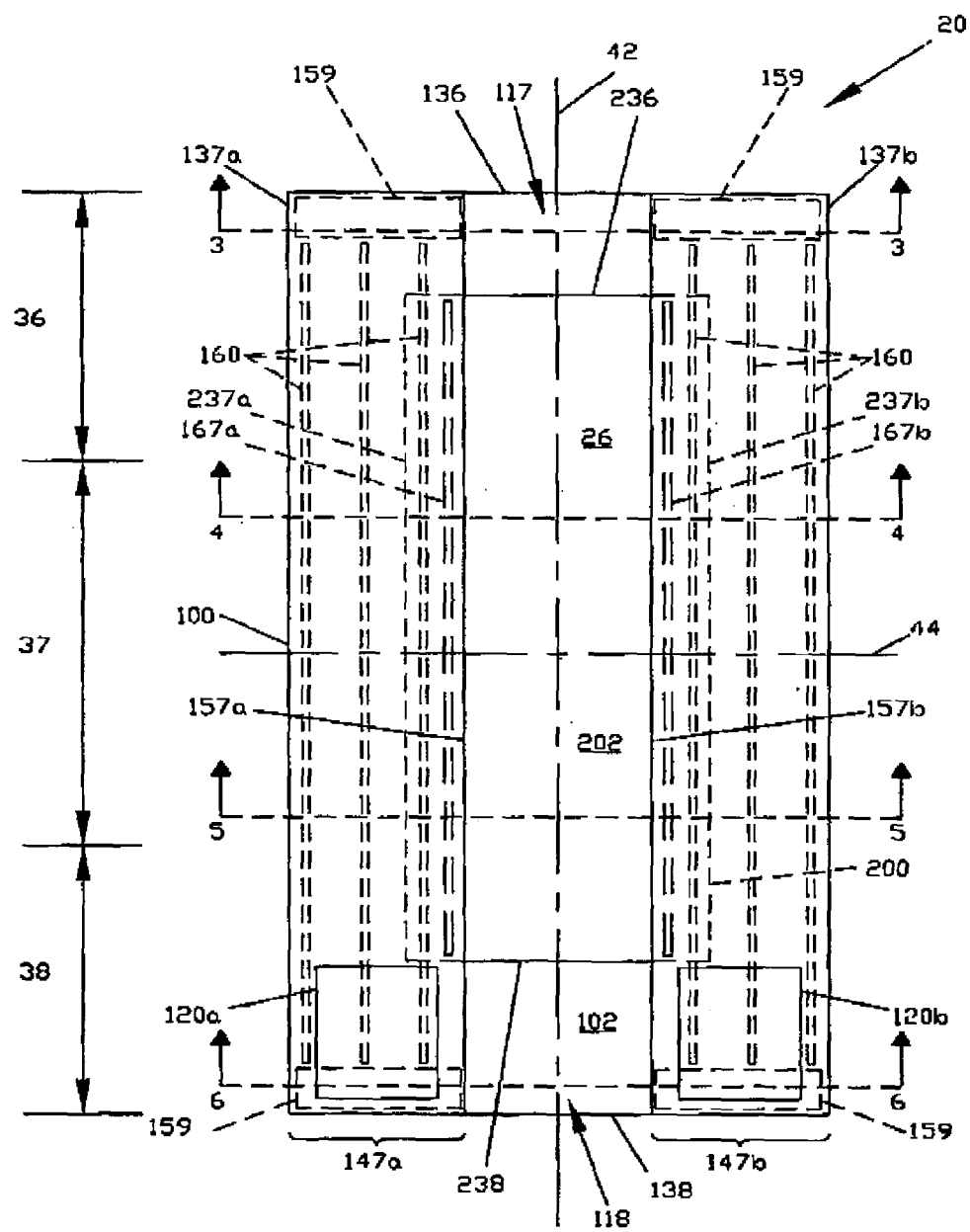
FIG. 1 is a plan view of an exemplary disposable absorbent article in the form of a diaper 20, which is shown in its flat, uncontracted state, i.e., without the contraction induced by elastic members.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45 degrees of the longitudinal direction are considered to be "longitudinal".

The term "lateral" refers to a direction running from a side edge to an opposing side edge of the article and generally at a right angle to the longitudinal direction. Directions within 45 degrees of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

In the following description and in the drawing figures, various structural elements are identified by reference numerals without suffixed letters when referring to the group as a whole and by the same reference numerals with suffixed letters when distinguishing between, for example, left and right members of the group. As an example, the side flaps as a group are identified by the reference numeral 147 while the individual left and right side flaps are respectively designated as elements 147a and 147b.

Description of Exemplary Diaper Embodiment

Reference is made to FIG. 1, FIG. 2, FIG. 3, FIG. 4, FIG. 5, FIG. 6, FIG. 7, FIG. 8, and FIG. 9 for this section of this description.

One end portion of the exemplary diaper 20 is configured as a front waist region 36. The longitudinally opposing end portion of the diaper 20 is configured as a back waist region 38. An intermediate portion of the diaper 20 extending longitudinally between the front waist region 36 and the back waist region 38 is configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The exterior surface 104 is intended to be placed toward any clothing that is worn over the diaper 20. The chassis 100 also has a longitudinal axis 42 and a lateral axis 44. The longitudinal axis 42 extends through the midpoint of the front waist edge 136 and through the midpoint of the back waist edge 138 of the chassis 100. The lateral axis 44 extends through the midpoint of the left side edge 137a and through the midpoint of the right side edge 137b of the chassis 100. The exemplary chassis 100 shown in FIG. 1 additionally has longitudinally extending and laterally opposing water vapor-permeable, i.e., breathable, side flaps 147a and 147b that are described in more detail below.

The basic structure of the diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237a, and right side edge 237b of the absorbent assembly 200 may lie inward of the respective front waist edge 136, back waist edge 138, left side edge 137a, and right side edge 137b of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

When the diaper 20 is worn on the lower torso of a wearer, the front waist edge 136 and the back waist edge 138 encircle the waist of the wearer, while at the same time the side edges 137a and 137b encircle the legs of the wearer. At the same time, the crotch region 37 is generally positioned between the legs of the wearer and the absorbent assembly 200 extends from the front waist region 36 through the crotch region 37 to the back waist region 38.

Description of the Chassis

In FIG. 10, FIG. 11, FIG. 12, and FIG. 13, the exemplary chassis 100 is shown laid out flat before the breathable side flaps 147a and 147b are formed by folding portions of the chassis 100 laterally inward, i.e., toward the longitudinal axis 42. In this condition of being laid out flat, the chassis 100 has a longitudinally extending left outer side edge 155a and a laterally opposing and longitudinally extending right outer side edge 155b. Both of these outer side edges extend longitudinally between the front waist edge 136 and the back waist edge 138. As is described in more detail below, when the breathable side flaps 147 are formed by folding portions of the chassis 100 laterally inward, the outer side edges 155 of the chassis form the proximal edges 157 of the side flaps.

The chassis 100 includes a water-impermeable center sheet 26 having a left side edge 126a and a right side edge 126b. Many suitable materials for use as the center sheet 26 are well-known, including films of polyethylene and other polyolefins. Multi-layer center sheets, such as laminates of a film and a nonwoven, are also well-known and may be suitable for use as the center sheet 26. Such a laminate center sheet may be oriented with the nonwoven disposed exteriorly to provide the feel and appearance of a more cloth-like outermost layer than would be provided by using the film as the outermost layer.

Figure 14:
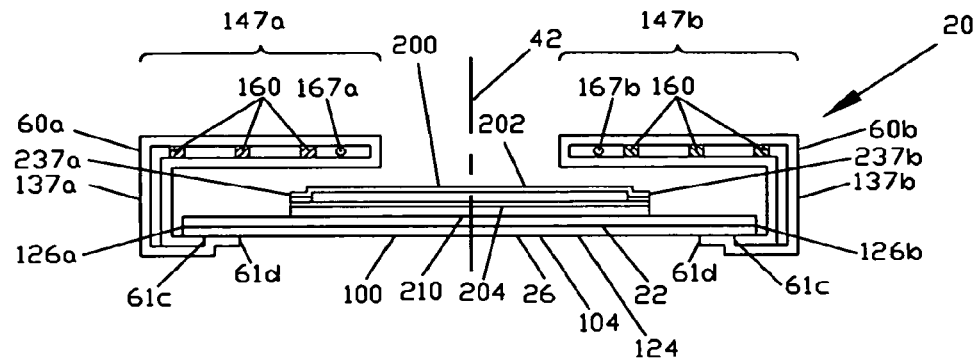
FIG. 14 is a section view of an alternative embodiment of the diaper 20 of FIG. 1 taken at the section line 4-4.
Figure 15:
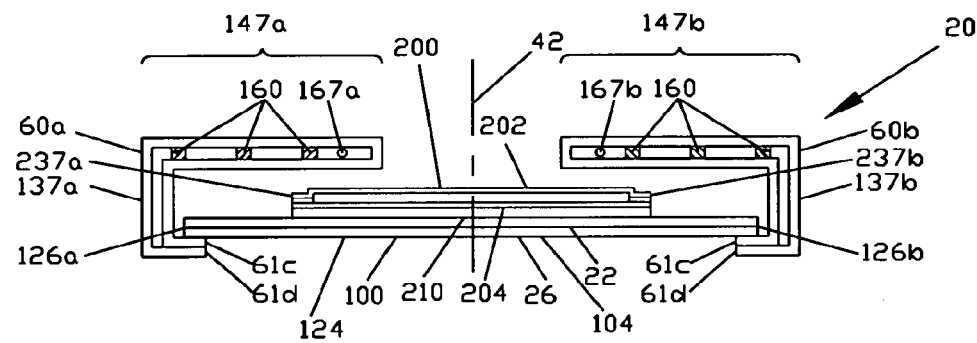
FIG. 15 is a section view of an alternative embodiment of the diaper 20 of FIG. 1 taken at the section line 4-4.
Figure 16:
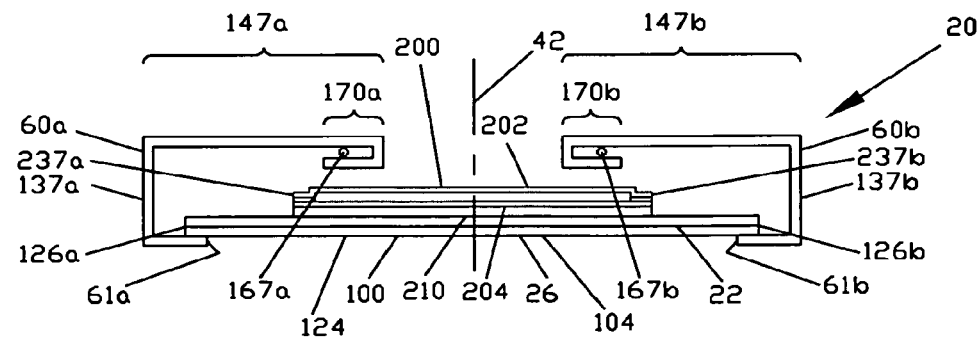
FIG. 16 is a section view of an alternative embodiment of the diaper 20 of FIG. 1 taken at the section line 4-4.

The chassis 100 may, but need not, additionally include an inner liner 22, as shown in FIG. 14, FIG. 15, and FIG. 16. The inner liner 22 may form a portion of the interior surface 102 of the chassis 100 that is intended to be placed against the body of the wearer. For example, the inner liner may cover and thereby lie interiorly of a portion or all of the absorbent assembly 200. The inner liner 22 preferably is formed of a soft material that will not irritate the skin of the wearer. Such an inner liner 22 may serve to isolate the skin of the wearer from a portion of the center sheet 26 as may be desirable, for example, when the diaper 20 is worn under conditions in which contact between the skin and a center sheet film could be uncomfortable. Many suitable materials for the inner liner 22 are well-known in the art, including rayon and synthetic nonwovens such as spunbonded or carded polypropylene or polyester.

The inner liner 22 may extend to the edges of the chassis 100. Alternatively, one or more of the edges of the inner liner 22 may lie inward of the edges of the chassis 100. For example, with reference to the exemplary diaper 20 shown in FIG. 1, only the portions of the center sheet 26 lying in the gaps between the front edge 236 of the absorbent assembly 200 and the front waist edge 136 of the chassis 100 and between the back edge 238 of the absorbent assembly 200 and the back waist edge 138 of the chassis 100 would need to be covered in order to isolate the skin of the wearer from the center sheet 26. Therefore, a laterally extending strip of the inner liner 22 disposed in the gap in the front waist region 36 and a similar laterally extending strip of the inner liner 22 disposed in the gap in the back waist region 38 may suffice.

The chassis 100 includes longitudinally extending laterally opposing side sheets 60 attached to the center sheet 26 adjacent to its side edges 126. For example, the side sheets may be attached to the center sheet by continuous, water impermeable bonds or seals made by any of several known methods, such as the application of adhesives, mechanical bonding, and thermal bonding, or a combination of known bonding methods.

When the exemplary chassis 100 is laid out flat, each side sheet 60 overlaps the center sheet 26 such that the proximal edge 61a of the left side sheet 60a lies laterally inward of the left side edge 126a of the center sheet 26 and the proximal edge 61b of the right side sheet 60b lies laterally inward of the right side edge 126b of the center sheet 26. Each side sheet 60 extends laterally outwardly from its proximal edge 61 past the respective side edge 126 of the center sheet 26 to its distal edge 62. Thus, the distal edges 62 of the side sheets 60 form the outer side edges 155 of the chassis 100 in this laid out flat condition.

Each side sheet 60 may be doubled over substantially its entire area, either by folding the side sheet or by adding a second layer to the side sheet. For example, as shown in FIG. 3, FIG. 4, FIG. 5, and FIG. 6, each side flap 147 may include two layers 63 and 64 of the respective doubled side sheet 60 and the respective flap elastic member may be sandwiched between the two layers. In this embodiment, the distal edge 62 of each side sheet 60 is formed where the side sheet is folded for doubling. The proximal edge 61 of each side sheet 60 is doubled by the doubling of the side sheet. Such a doubled side sheet 60 may be attached to the interior surface 122 of the center sheet 26 adjacent to the proximal edge 61c of its first layer 63 and attached to the exterior surface 124 of the center sheet 26 adjacent to the proximal edge 61d of its second layer 64 as shown in FIG. 3, FIG. 4, FIG. 5, and FIG. 6.

Alternatively, such a doubled side sheet 60 may be attached to either the exterior surface 124 or the interior surface 122 of the center sheet 26 adjacent to both of its proximal edges 61. For example, each of the doubled side sheets 60 shown in FIG. 14 is attached to the exterior surface 124 of the center sheet 26 adjacent to both of its proximal edges 61. Another example is shown in FIG. 15, in which each of the doubled side sheets 60 is attached to the exterior surface 124 of the center sheet 26 adjacent to the proximal edge 61c of its first layer 63 and also attached to itself adjacent to both the proximal edge 61c of its first layer 63 and the proximal edge 61d of its second layer 64 by overlapping its second layer 64 onto its first layer 63.

The layers of each doubled side sheet 60 may remain unattached to each other and thus free to contact each other or separate from each other. Alternatively, the layers of each doubled side sheet 60 may be attached together laterally continuously or intermittently between the proximal edges 61 and the proximal edge 157 of the side flap 147. For example, the layers of each doubled side sheet 60 may be attached together by adhesives, mechanical bonds, or thermal bonds, or by a combination of known bonding methods.

In the exemplary embodiment shown in FIG. 1, FIG. 2, FIG. 4, and FIG. 5, the layers are attached together in laterally spaced attachment zones 160 extending longitudinally through the crotch region 37 and into the waist regions 36 and 38. Such longitudinally extending attachment together prevents the layers from separating and thereby presenting an undesirable baggy or blousy appearance around the legs of the wearer, as well as tending to stiffen the side flaps 147 slightly and thereby helping to ensure their proper fit against the body.

Alternatively, or in addition, the layers of the each doubled side sheet 60 may be attached together in the waist regions 36 and 38 adjacent to the waist edges 136 and 138, for example in laterally extending attachment zones 159 as shown in FIG. 1, FIG. 2, FIG. 3, and FIG. 6. This lateral attachment may be laterally intermittent or laterally continuous. When such laterally extending attachment is continuous, it prevents the layers from separating and thereby presenting an undesirable unfinished appearance at the waist edges, as well as preventing the leakage at the waist edge of any liquid waste from between the layers.

Alternatively, each side sheet 60 may have the form of a single layer. For example, as shown in FIG. 16, a side sheet 60 may be attached adjacent to its proximal edge 61 onto either the interior surface 122 or the exterior surface 124 of the center sheet 26 and incorporated into a side flap 147. In this embodiment, the side flap 147 includes only a single layer of the side sheet 60 everywhere except along the proximal edge 157 of the side flap, where the side sheet is doubled to form a folded hem 170 to sandwich a flap elastic member.

Exemplary materials suitable for use in the side sheets 60 include polyolefinic films, microporous or other breathable formed films, breathable monolithic films, and hydrophobic nonwovens. Suitable hydrophobic nonwovens include SM (spunbond meltblown), SMS (spunbond meltblown spunbond), and SMMS (spunbond meltblown meltblown spunbond) composites. The materials of the water vapor-permeable side sheets may be selected to balance overall product economics and function. For example, a relatively more expensive nonwoven material having a relatively high basis weight may provide an acceptable level of water-impermeability for use in a single layer side flap construction. Alternatively, a relatively less expensive nonwoven having a relatively lower basis weight may provide the requisite level of water-impermeability only if it is doubled, thereby requiring a relatively greater area of material. As another example, a microporous film may provide a relatively optimal combination of water-impermeability and material cost.

Figure 19:
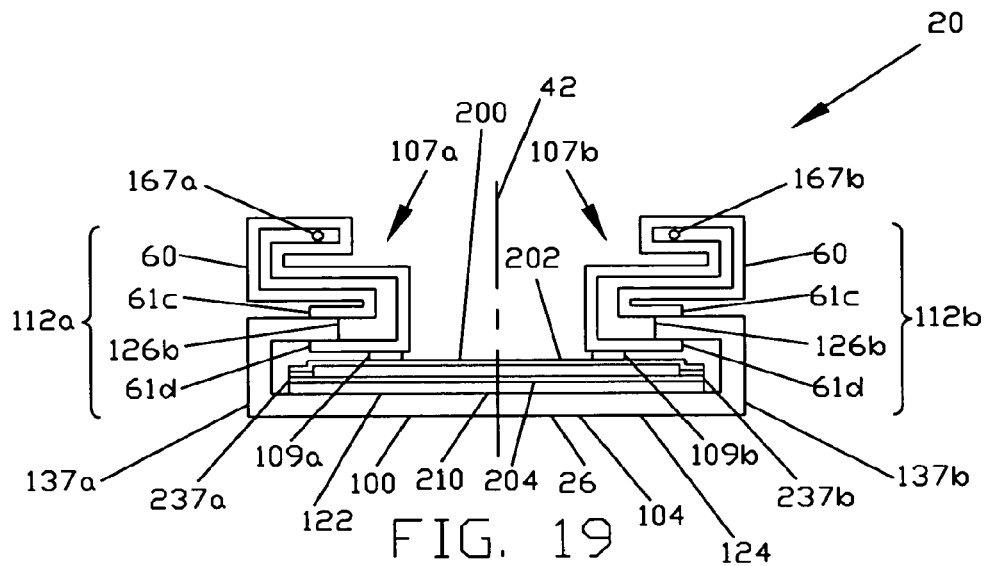
FIG. 19 is a section view of the diaper 20 of FIG. 18 taken at the section line 19-19.

As shown in FIG. 1, FIG. 2, FIG. 3, FIG. 4, FIG. 5, and FIG. 6, the exemplary chassis 100 has longitudinally extending and laterally opposing breathable side flaps 147a and 147b that are disposed on the interior portion of the diaper 20 that faces inwardly toward the wearer and contacts the wearer. The side flaps are formed by folding portions of the chassis 100 including the water vapor-permeable side sheets 60 laterally inward, i.e., toward the longitudinal axis 42, to form both the respective side flaps 147a and 147b and the side edges 137a and 137b of the chassis 100. The side sheets 60 of the chassis 100 may be folded laterally inward as shown in FIG. 1, FIG. 2, FIG. 3, FIG. 4, FIG. 5, and FIG. 6 to form the side flaps. Alternatively, the chassis may be folded such that each side flap includes the respective side sheet 60 and a portion of the center sheet 26, as shown in FIG. 19. In either configuration, at least a portion of each side flap is breathable due to its inclusion of at least a portion of the respective water vapor-permeable side sheet.

The chassis 100 may simply be folded loosely or may be creased along a portion of each of its side edges 137. For example, it may be desirable to form creases along portions of the side edges 137 in the crotch region 37 in order to impart a more finished appearance to the diaper 20. Alternatively or in addition to creasing, a portion of each of the folded side flaps 147 adjacent to the side edges 137 may be attached to the interior surface 102 of the chassis 100 to achieve a similar result.

Each side flap 147 has a proximal edge 157. In the exemplary diaper 20 shown in FIG. 1, the side flaps 147 overlap the absorbent assembly 200, i.e., the proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200, i.e., the proximal edges 157 may lie laterally outward of the respective side edges 237 of the absorbent assembly 200.

In the exemplary chassis 100 shown in FIG. 1, the side flaps 147 extend the full length of the chassis 100 between the front waist edge 136 and the back waist edge 138. Such a full length configuration may be desirable in order to minimize the amount of waste material and the difficulty associated with the manufacture of the diaper 20, especially when the method used to manufacture the diaper 20 requires the introduction of the material or materials for the chassis 100 in the form of a continuous web or multiple continuous webs. Alternatively, the side flaps may be shorter and extend less than the full distance between the front waist edge 136 and the back waist edge 138. Such a shorter configuration may be desirable in order to minimize the total amount of material used in the manufacture of the diaper 20.

Each of the breathable side flaps 147 is attached to the interior surface 102 of the chassis 100 in attachment zones located in the front waist region 36 and in the back waist region 38. For example, in the chassis 100 shown in FIG. 1, the side flaps 147 are attached to the interior surface 102 of the chassis 100 in the adhesive attachment zones that are shown there and that are more clearly visible in FIG. 10, where the chassis 100 is shown laid out flat before the side flaps 147 are formed. In particular, each side flap 147 is attached to the interior surface 102 of the chassis 100 in an attachment zone 153 adjacent to the front waist edge 136 and in a longitudinally opposing attachment zone 154 adjacent to the back waist edge 138. The attachment zones may have equal areas or may be unequal in area. For example, the front attachment zones 153 may be of one size and the back attachment zones 154 may be of another size.

Alternatively, each attachment zone may extend laterally across the full width of the respective side flap. For example, a laterally oriented adhesive attachment zone may extend laterally from the chassis side edge 137 to the side flap proximal edge 157 and thereby attach the entire width of the side flap 147 adjacent to the front waist edge 136 to the interior surface 102 of the chassis 100. In embodiments in which the front edge 236 or the back edge 238 of the absorbent assembly 200 coincides with the respective front waist edge 136 or back waist edge 138 of the chassis 100 and the side flaps 147 overlap the absorbent assembly 200, the side flaps 147 may be attached to the absorbent assembly 200 instead of, or in addition to, being attached to the interior surface 102 of the chassis 100.

Between the attachment zones, the proximal edges 157 of the side flaps 147 remain free, i.e., are not attached to the interior surface 102 of the chassis 100 or to the absorbent assembly 200. Also between the attachment zones, each breathable side flap preferably includes a longitudinally extensible flap elastic member that is attached adjacent to the proximal edge of the side flap by any of many well-known means. Each such flap elastic member may be attached over its entire length or over only a portion of its length. For example, such a flap elastic member may be attached only at or near its longitudinally opposing ends and may be unattached at the middle of its length. Such a flap elastic member may be disposed in the crotch region 37 and may extend into one or both of the front waist region 36 and the back waist region 38. For example, in the exemplary chassis 100 shown in FIG. 1, an elastic strand 167a is attached adjacent to the proximal edge 157a of the left side flap 147a and extends into both the front waist region 36 and the back waist region 38. Similarly, an elastic strand 167b is attached adjacent to the proximal edge 157b of the right side flap 147b and extends into both the front waist region 36 and the back waist region 38.

Each flap elastic member may be enclosed inside a folded hem. For example, in the exemplary chassis 100 shown in FIG. 4 and FIG. 5, each elastic strand 167 is enclosed inside a hem 170 formed adjacent to the proximal edge 157 of the respective side flap 147. Alternatively, the flap elastic member may be sandwiched between two layers of the chassis, e.g., between the layers of the side flap or between the side flap and a separate material such as an inner liner. As another alternative, the flap elastic member may be attached on a surface of the chassis 100 and remain exposed.

When stretched, the flap elastic member adjacent to each side flap edge allows the side flap edge to extend to the flat uncontracted length of the chassis, e.g., the length of the chassis 100, as shown in FIG. 1. When allowed to relax, the flap elastic member contracts to gather the portion of the side flap edge along which the flap elastic member is attached and thereby make the relaxed length of the side flap edge less than the flat uncontracted length of the chassis. Thus, when the exemplary diaper 20 is in a relaxed condition, each elastic strand 167 contracts to gather the proximal edge 157 of the respective side flap 147. The contractive forces of the elastic strands 167 are transmitted at the respective front attachment zones 153 to the interior surface 102 of the chassis 100 at the front waist region 36. Similarly, the contractive forces of the elastic strands 167 are transmitted at the respective back attachment zones 154 to the interior surface 102 of the chassis 100 at the back waist region 38. These contractive forces pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because the proximal edge 157 remains free between the attachment zones, the contractive force of the elastic strand 167 lifts the proximal edge 157 away from the interior surface 102 of the chassis 100. This lifting of the proximal edges 157 when the diaper 20 is in the relaxed condition lifts the side flaps 147 into position to serve as side barriers adjacent to the side edges 237 of the absorbent assembly 200.

When the diaper 20 is worn, the relaxed "U" shape generally conforms to the body of the wearer such that the front waist region 36 and the back waist region 38 can be fastened together to encircle the waist and the legs of the wearer. When the diaper 20 is worn in this manner, the elastic strands 167 tend to hold the lifted proximal edges 157 of the side flaps 147 in contact with the body of the wearer and thereby form seals to help prevent the leakage of deposited bodily waste out of the diaper 20. The lateral spacing of the lifted proximal edges 157 is selected to allow the deposit of bodily wastes from the lower torso of the wearer into the space between the lifted side flaps 147 and thereby directly onto the absorbent assembly 200. The width of each of the side flaps 147 in effect becomes its height when the free portion of its proximal edge is lifted and the side flap serves as a side barrier to leakage. This height preferably is selected to allow the lifted proximal edges 157 to fit into the leg creases of the body of the wearer at the same time as the absorbent assembly 200 is held in contact with the body.

Figure 2:
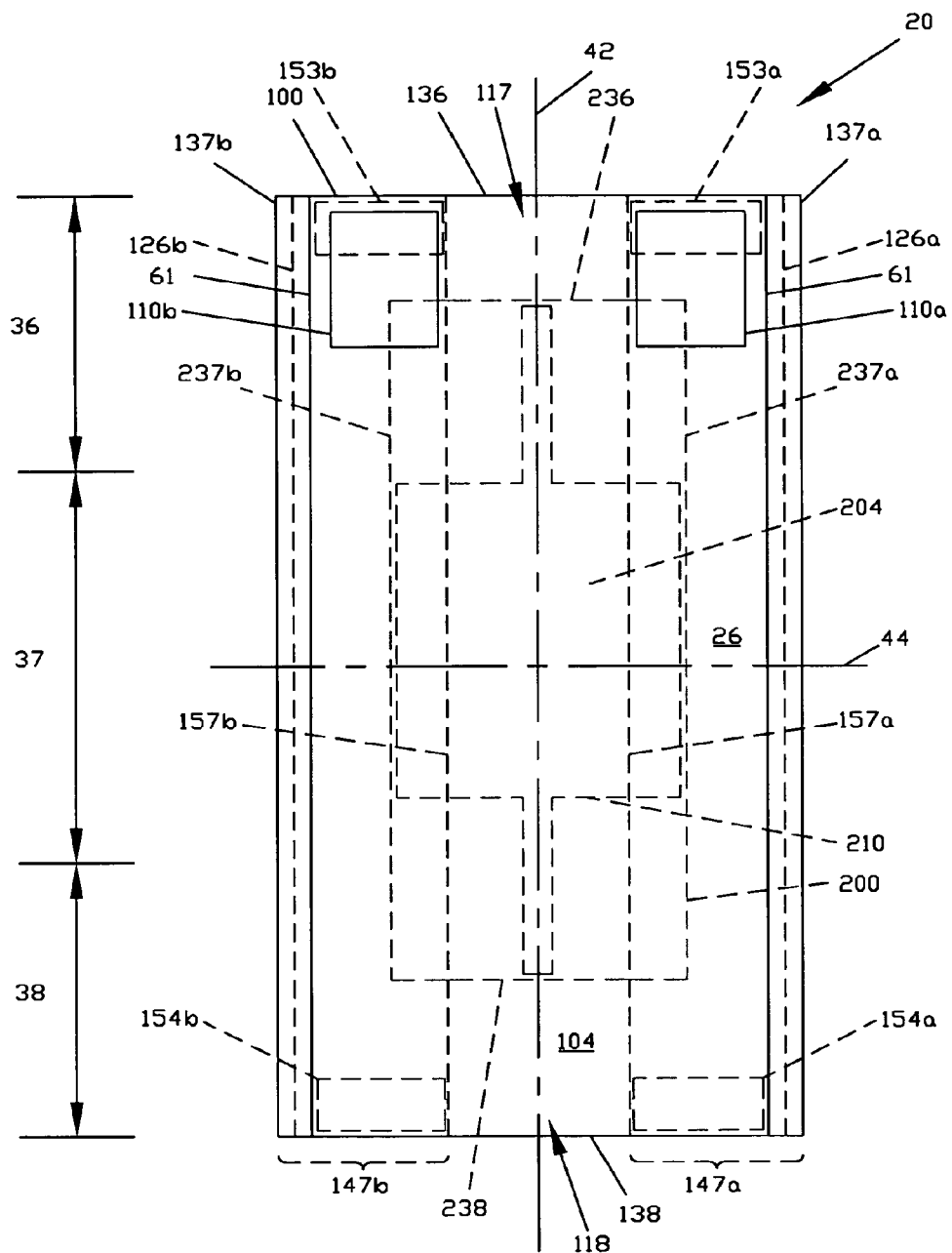
FIG. 2 is a plan view of the diaper 20 of FIG. 1 in its flat, uncontracted state, with the exterior portion of the diaper 20 that faces outwardly away from the wearer shown facing the viewer.

In the finished diaper, the chassis may have a generally rectangular shape, as in the exemplary diaper 20 shown in FIG. 1 and FIG. 2. Such a generally rectangular configuration may be desirable in order to minimize the amount of waste material and the difficulty associated with the manufacture of the diaper 20. Alternatively, the chassis may have side edges 137a and 137b that are not straight, but instead are curved and/or notched, thereby giving an overall shape in plan view of an hourglass or of an "I" to the diaper 20. This shape may help to conform the diaper 20 to the contour of the wearer's body in use. Such a shape may also be desirable in order to impart a tailored appearance to the diaper 20 when it is worn and/or to impart an impression that the diaper 20 will fit comfortably between the legs of a wearer. Any one of many well-known ways may be used to form a non-rectangular configuration of the chassis. For example, laterally distal portions may be removed from the chassis to make its lateral dimension at and adjacent to the lateral axis 44 smaller than its lateral dimension at and adjacent to the front waist edge 136 and smaller than its lateral dimension at and adjacent to the back waist edge 138, i.e., to make the chassis narrower in the crotch region 37 than at the waist edges 136 and 138. Alternatively, a portion of each of the side edges 137a and 137b may be folded laterally inward in order to achieve the same result. Such folded portions of the side edges 137a and 137b may be creased or attached, or both creased and attached, in order to prevent their unfoldment.

Figure 17:
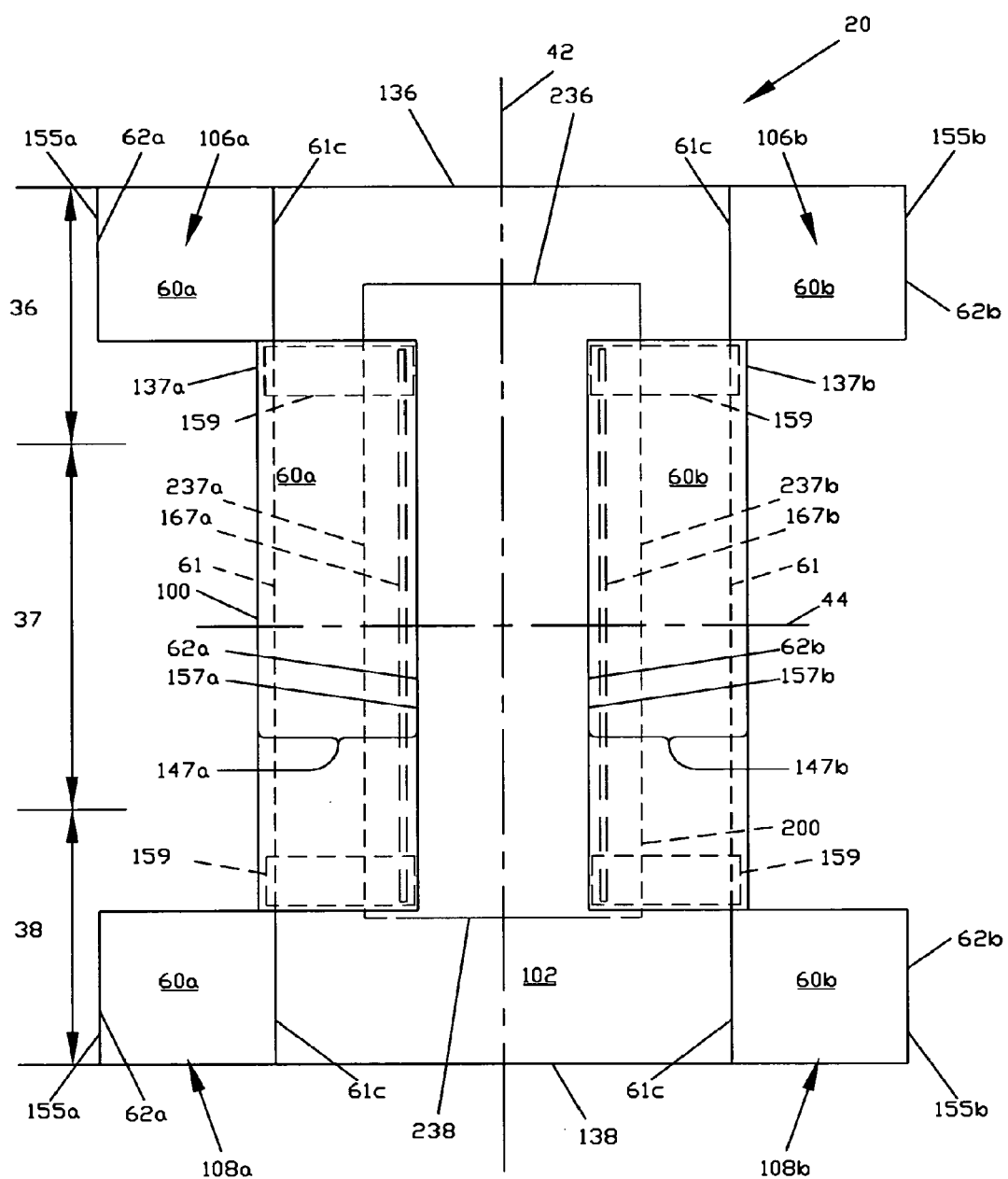
FIG. 17 is plan view of an exemplary diaper 20 shown in its flat, uncontracted state, i.e., without the contraction induced by elastic members, in which portions of the chassis are left laid out flat when other portions are folded laterally inward to form the side flaps 147a and 147b.

An exemplary form of a non-rectangular configuration of the chassis is shown in FIG. 17. As shown in this figure, portions of the chassis extending laterally between the outer side edges and the respective side edges in one or both of the waist regions may be left laid out flat, i.e., may remain unfolded, when other portions are folded laterally inward to form the side flaps. For example, as shown in FIG. 17, the portions 106a and 106b extending longitudinally from the front waist edge 136 toward the lateral axis 44 in the front waist region 36 and extending laterally between each of the outer side edges 155 and the respective side edges 137 may be left laid out flat, i.e., may remain unfolded. Similarly, the portions 108a and 108b extending longitudinally from the back waist edge 138 toward the lateral axis 44 in the back waist region 38 and extending laterally between each of the outer side edges 155 and the respective side edges 137 may be left laid out flat, i.e., may remain unfolded. Other portions extending longitudinally between the portions that remain unfolded and through the crotch region 37 may be folded laterally inward to form the side flaps 147. The portions 106 and the portions 108 form "ears" that project laterally outward from each of the waist regions of the diaper. These ears project laterally outward beyond the inward-folded portions and impart an "I" shape to the diaper, as shown in FIG. 17. It is not necessary that portions remain unfolded at both ends as shown in FIG. 17. For example, the portions 106 in the front waist region 36 may remain unfolded and only the portions 108 in the back waist region 38 may be folded laterally inward, or vice versa, in some embodiments.

An alternative way to form an "I"-shaped non-rectangular configuration of the chassis as shown in FIG. 17 is to form the chassis in the "I" shape and attach an additional layer or layers to the interior surface of the "I"-shaped chassis at or adjacent to each of the side edges 137 of the chassis 100 to form the respective side flaps 147. In embodiments in which the side flaps are formed by attaching an additional layer or layers to the chassis, each of the additional layer or layers may be attached at or adjacent to its laterally distal edge.

Figure 3:
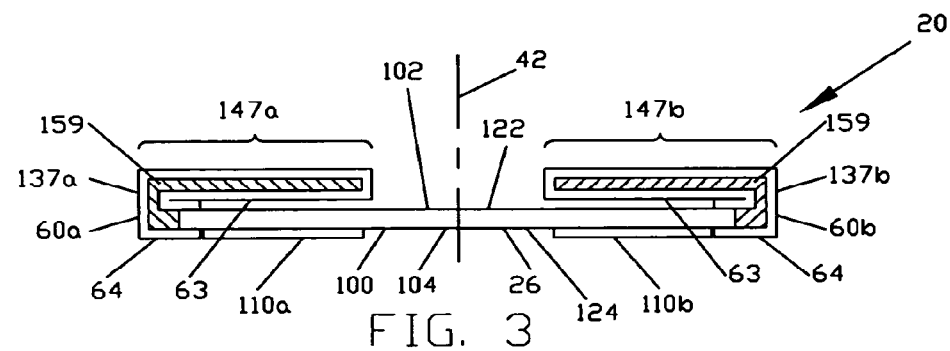
FIG. 3 is a section view of the diaper 20 of FIG. 1 taken at the section line 3-3.
Figure 4:
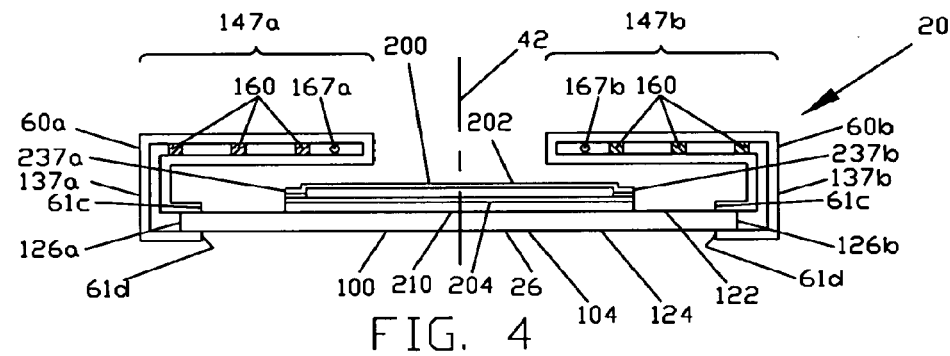
FIG. 4 is a section view of the diaper 20 of FIG. 1 taken at the section line 4-4.
Figure 5:
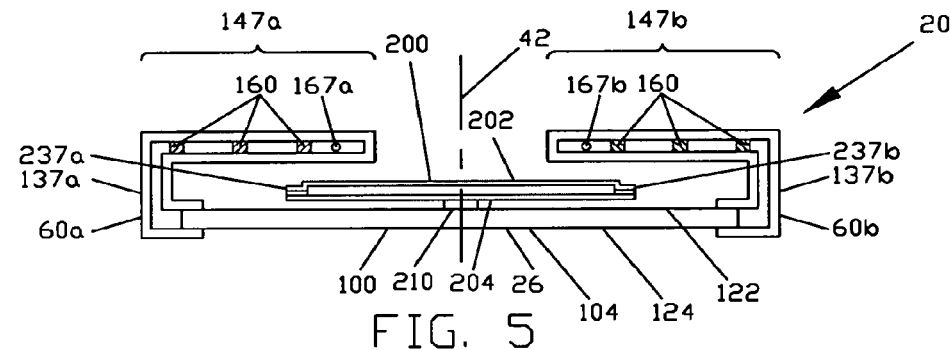
FIG. 5 is a section view of the diaper 20 of FIG. 1 taken at the section line 5-5.
Figure 6:
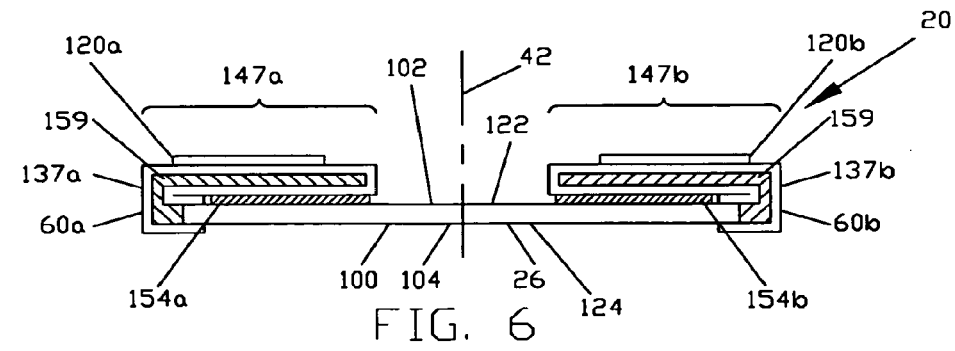
FIG. 6 is a section view of the diaper 20 of FIG. 1 taken at the section line 6-6.
Figure 7:
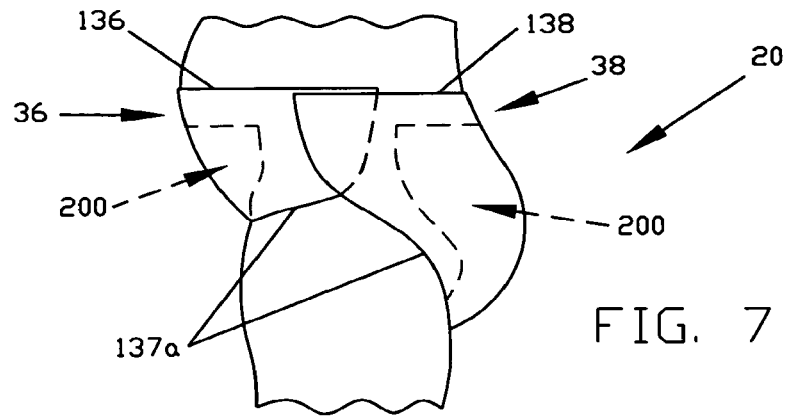
FIG. 7 is a simplified side elevation view of an exemplary diaper 20 being worn about a lower torso of a wearer.
Figure 8:
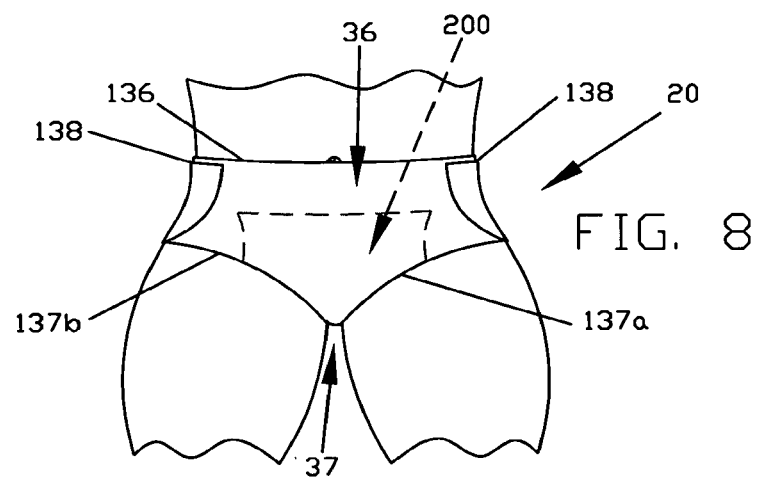
FIG. 8 is a front elevation view of the diaper 20 of FIG. 7 being worn about the lower torso of the wearer.
Figure 9:
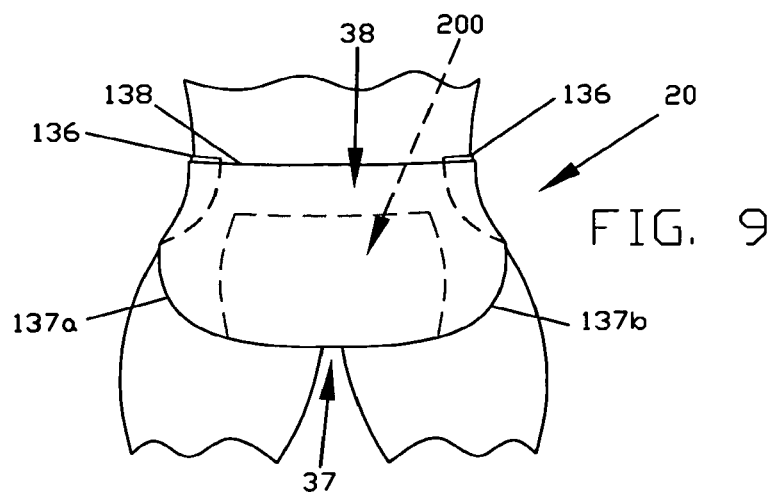
FIG. 9 is a back elevation view of the diaper 20 of FIG. 7 being worn about the lower torso of the wearer.
Figure 10:
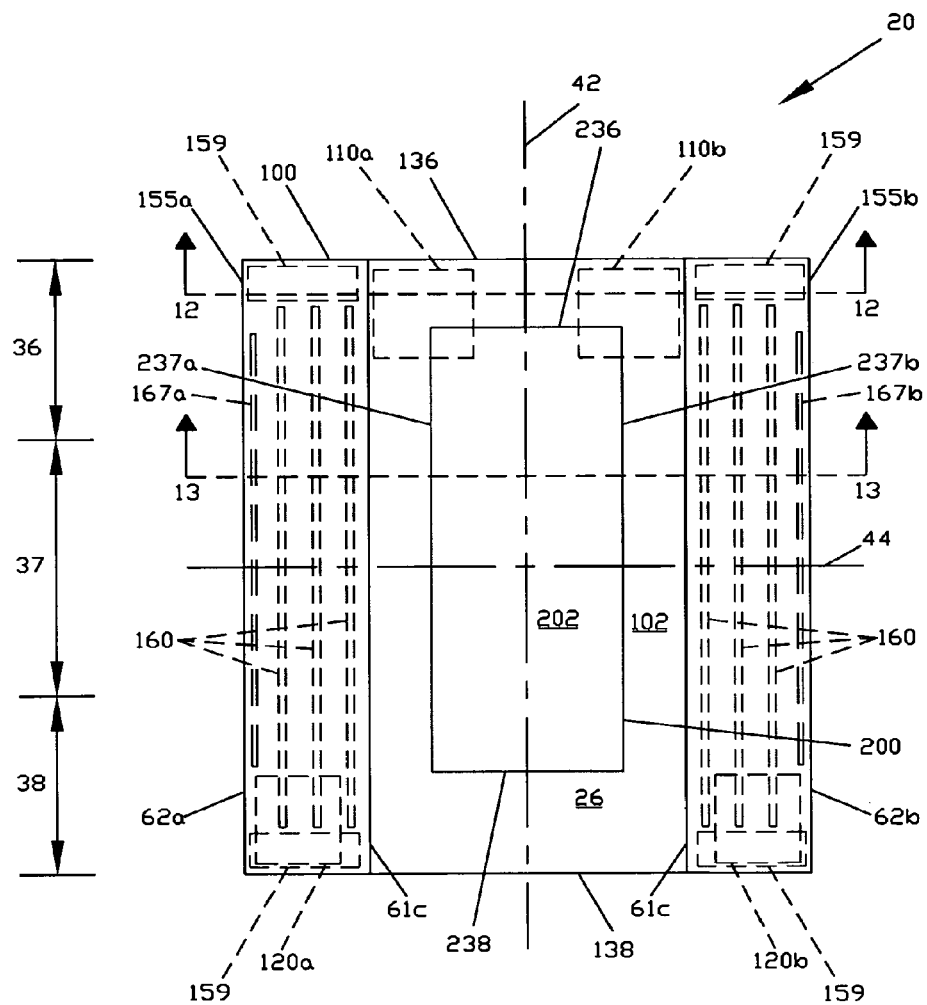
FIG. 10 is a plan view of an exemplary diaper 20 shown in its flat, uncontracted state, i.e., without the contraction induced by elastic members, before the side flaps 147a and 147b are formed by folding portions of the chassis 100 laterally inward, i.e., toward the longitudinal axis 42.
Figure 11:
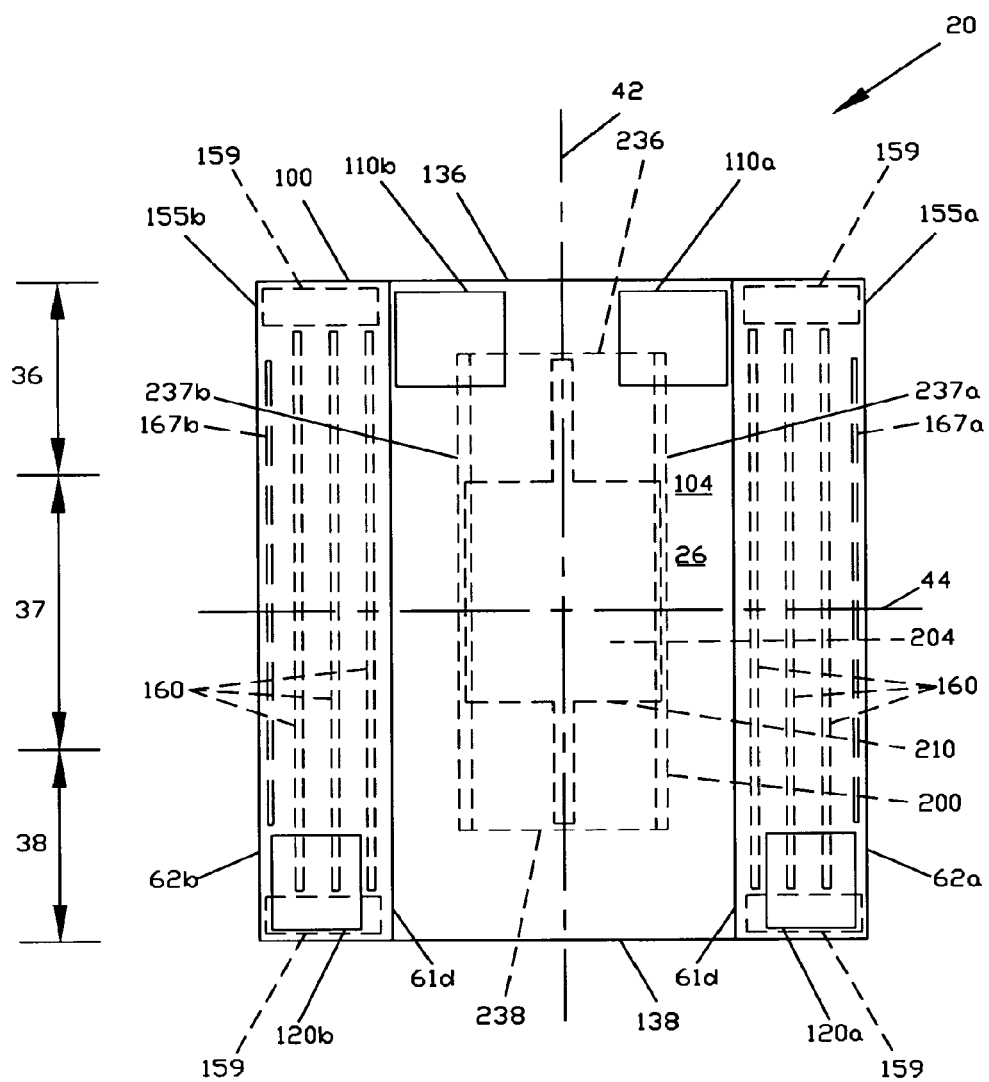
FIG. 11 is a plan view of the diaper 20 of FIG. 10 in its flat, uncontracted state, with the exterior portion of the diaper 20 that faces outwardly away from the wearer shown facing the viewer.
Figure 12:
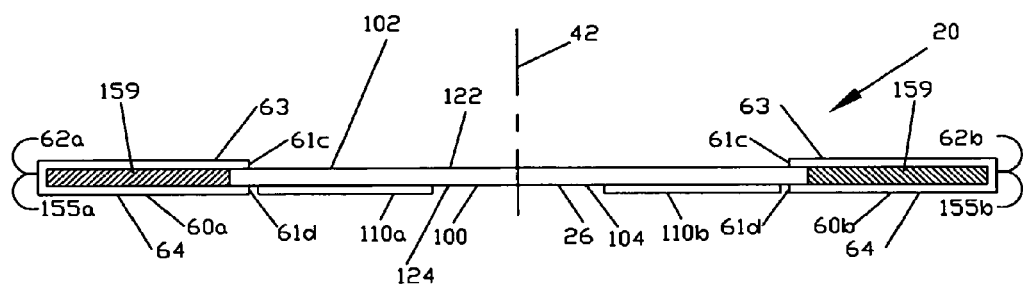
FIG. 12 is a section view of the diaper 20 of FIG. 10 taken at the section line 12-12.
Figure 13:
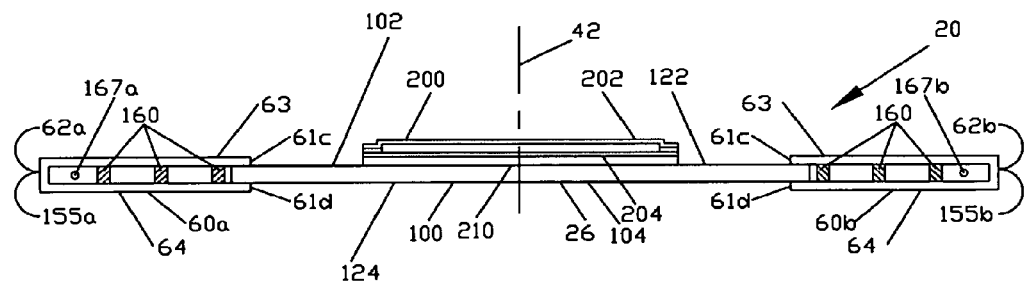
FIG. 13 is a section view of the diaper 20 of FIG. 10 taken at the section line 13-13.
Figure 18:
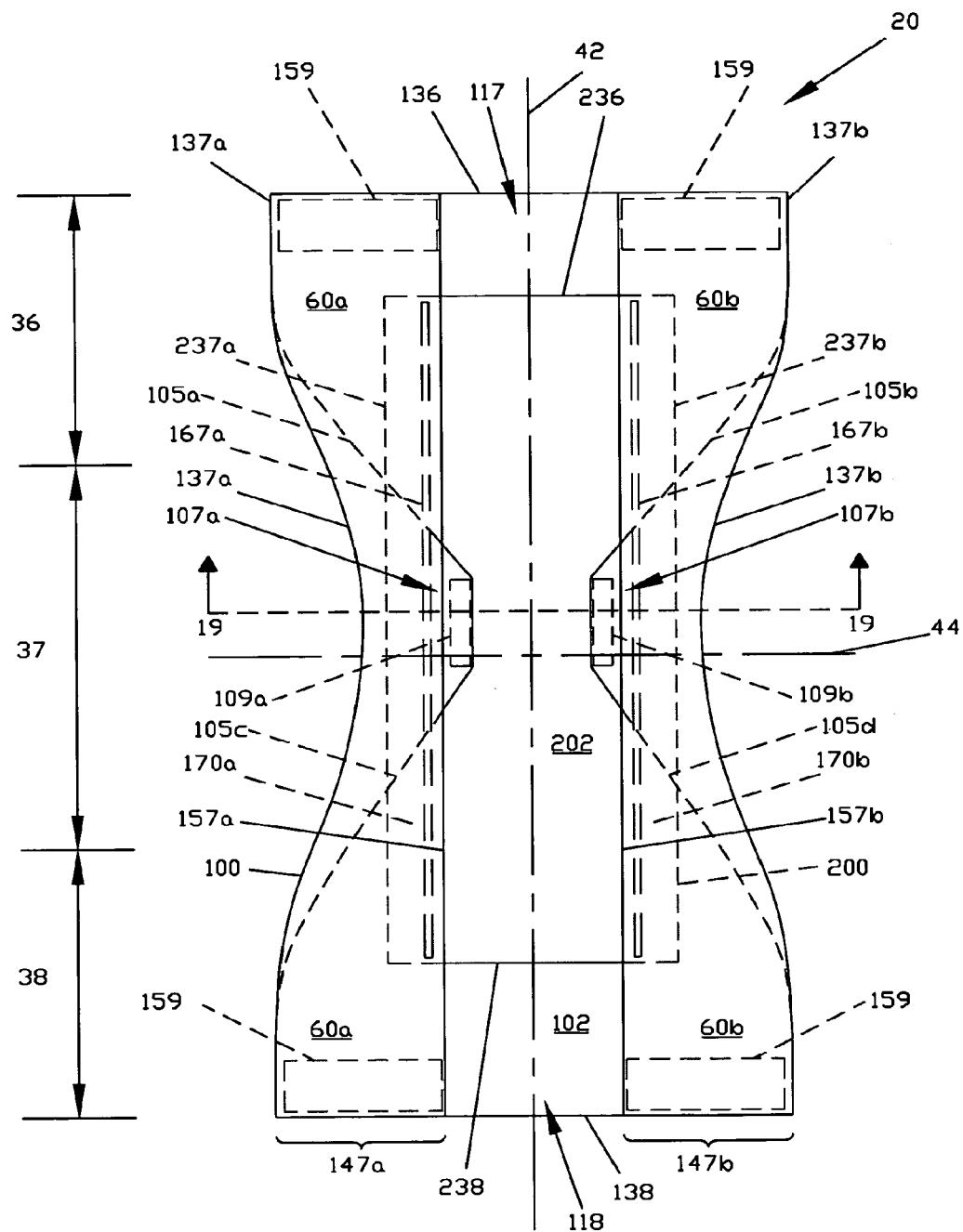
FIG. 18 is a plan view of an exemplary diaper 20 shown in its flat, uncontracted state, i.e., without the contraction induced by elastic members, in which portions of the chassis are folded over and attached to the interior surface of the absorbent assembly to impart an hourglass shape to the diaper 20.

Another exemplary way to form a non-rectangular configuration of the chassis is shown in FIG. 18 and FIG. 19. As shown in these figures, laterally opposing portions 107a and 107b of the chassis between each of the side edges 137 and the respective proximal edges 157 of the side flaps 147 may be folded laterally inward in the crotch region 37 along respective diagonal fold lines 105a, 105b, 105c, and 105d such that each of the folded portions 107 of the chassis overlaps the absorbent assembly 200 in the crotch region 37. The interior surface 102 of each of the folded portions 107 may be attached to the interior surface 202 of the absorbent assembly in the crotch region 37 at attachment zones 109a and 109b. This folding and attachment forms "W" shaped folds 112a and 112b in the chassis in the crotch region 37 as shown in FIG. 19, while retaining the configuration of the waist regions 36 and 38 as shown in FIG. 3 and FIG. 6. The overall effect on the shape of the chassis is to form an hourglass-shaped configuration as shown in FIG. 18. The attachment zones 109 may be disposed symmetrically with respect to either or both of the longitudinal axis 42 and the lateral axis 44. Alternatively, the attachment zones 109 may be disposed asymmetrically with respect to either or both of the longitudinal axis 42 and the lateral axis 44. For example, the attachment zones 109a and 109b shown in FIG. 18 are disposed symmetrically with respect to the longitudinal axis 42 and asymmetrically with respect to the lateral axis 44. In particular, the attachment zones 109a and 109b shown in FIG. 1 are disposed asymmetrically toward the front waist region 36.

Alternatively, the laterally opposing portions 107a and 107b of the chassis may be folded laterally inward in one or both of the waist regions in addition to being folded laterally inward in the crotch region. For example, in order to simplify the manufacture of the diaper, the laterally opposing portions 107a and 107b of the chassis may be folded laterally inward over their entire longitudinal lengths. The interior surface 102 of each of the folded portions 107a and 107b may be attached to the interior surface 202 of the absorbent assembly in the crotch region 37 at attachment zones 109a and 109b. This folding and attachment forms "W" shaped folds 112a and 112b in the chassis as shown in FIG. 19 over the entire longitudinal lengths of the laterally opposing portions 107a and 107b of the chassis. An hourglass shape may subsequently be imparted to the chassis when the laterally opposing portions are laterally extended by unfolding at their longitudinally distal ends to prepare the disposable diaper for use in the configuration shown in FIG. 18.

A portion or the whole of the chassis 100 may be made extensible to a degree greater than the inherent extensibility of the material or materials from which the chassis is made. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to encircle the waist of an individual wearer whose waist circumference falls within a predefined range, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer larger than the smaller diaper would fit. In other words, a lesser amount of material is needed in order to make a diaper capable of being properly fit onto a given size of a wearer when the material is made extensible as described. The portion of the chassis in one of the waist regions may be made laterally extensible to a maximum extensibility greater than a maximum extensibility of another portion of the chassis in the crotch region such that a lateral extension of each of the portions to its maximum extensibility imparts an hourglass shape to the chassis.

Additional extensibility in the chassis 100 in the lateral direction is relatively more useful than additional extensibility in the longitudinal direction because the abdomen of the wearer is likely to expand when the wearer changes posture from standing to sitting and the corresponding abdominal expansion increases the circumference that is encircled by the waist edges of the chassis 100, necessitating the lateral extension of the waist region or regions.

Figure 20:
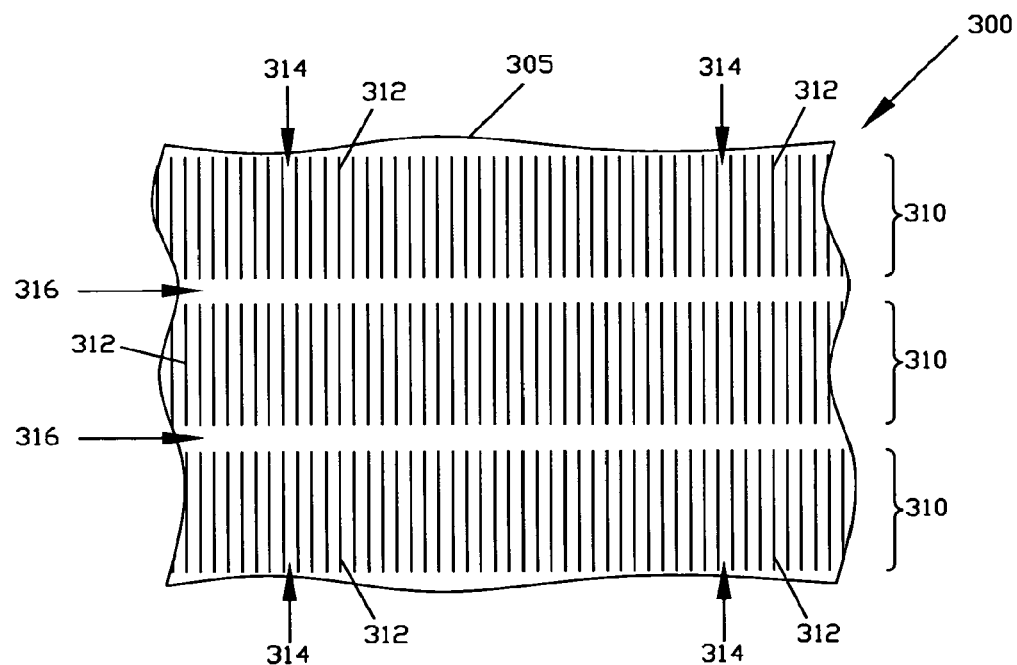
FIG. 20 is a plan view of an exemplary fragment of a formed web material.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 20. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

The front laterally central portion 117 and the back laterally central portion 118 of the chassis 100 between the attachment zones 153 and 154 may have a different range of extensibility from the portions of the chassis in the attachment zones. Additionally or alternatively, the laterally central portions 117 and 118 may be extensible to a greater or lesser degree when subjected to a given level of opposing tensile forces, i.e., may be more easily or less easily extensible, than the portions of the chassis in the attachment zones. For example, if the chassis is made uniformly extensible across its entire width prior to the formation of the side flaps, the double layering in the areas of the attachment zones after the formation of the side flaps may have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis may be deformed to a greater or a lesser degree than the altered regions in the attachment zones to render the laterally central portions more easily or less easily extensible than the respective portions in the attachment zones.

The front waist region 36 and the back waist region 38 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. These incorporated fastening elements may project laterally outward, i.e., away from the longitudinal axis 42 beyond one or both of the side edges 137a and 137b and/or may project longitudinally outward, i.e., away from the lateral axis 44 beyond one or both of the waist edges 136 and 138 or they may lie entirely inside the edges of the diaper 20.

Figure 21:
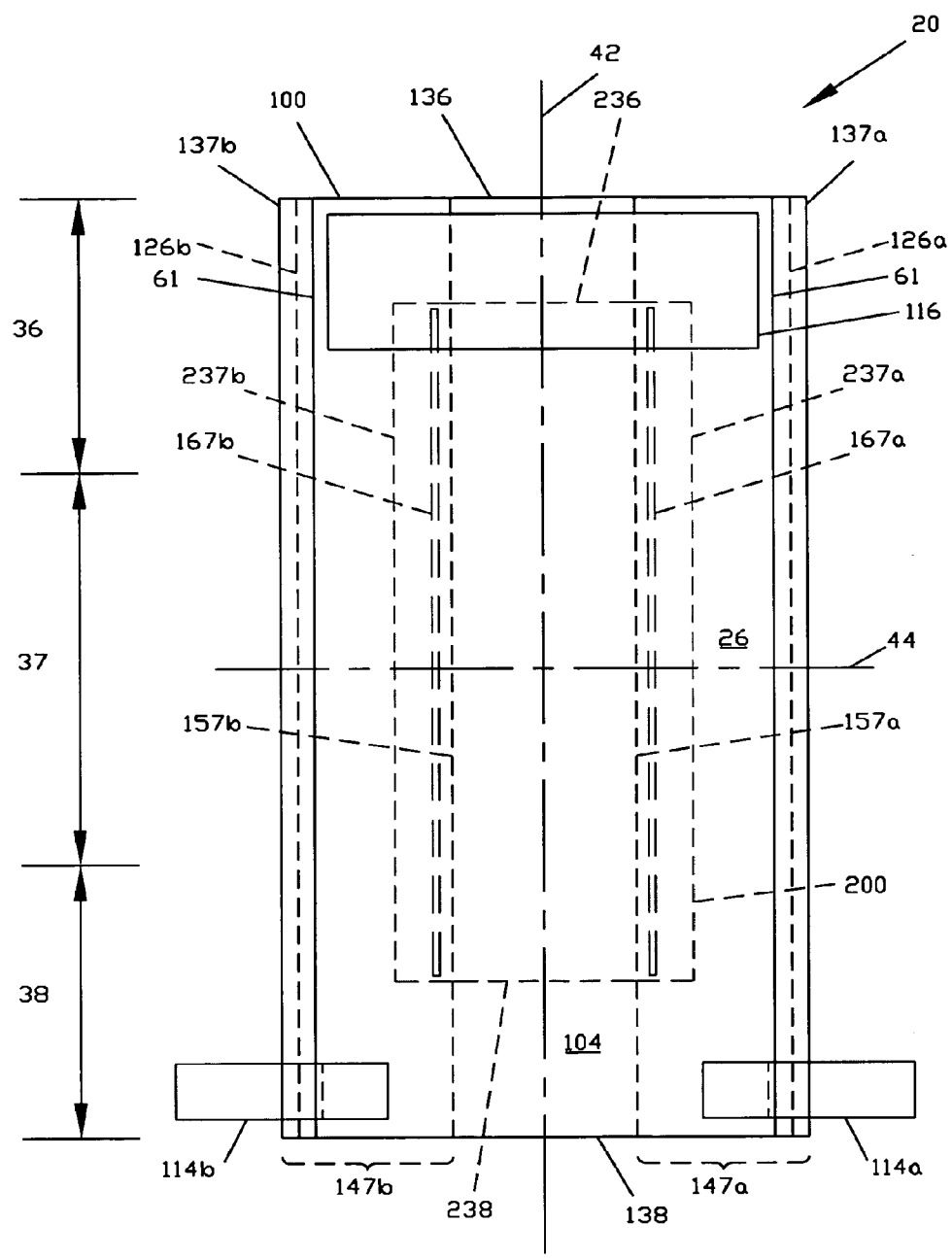
FIG. 21 is a simplified plan view of an exemplary disposable absorbent article in the form of a diaper 20, which is shown in its flat, uncontracted state, i.e., without the contraction induced by elastic members, having adhesive tape tabs 114a and 114b and a fastening surface 116 attached to the chassis.

For example, as shown in FIG. 21, laterally opposing adhesive tape tabs 114a and 114b may be attached to the chassis 100 at or adjacent to the side edges 137a and 137b of the diaper 20. The adhesive tape tabs 114a and 114b shown in FIG. 21 project laterally outward from the respective side edges 137a and 137b in the back waist region 38. In use, the adhesive tape tabs 114a and 114b shown in FIG. 21 may be adhered to the exterior surface 104 of the chassis 100 in the front waist region 36 to fasten the back waist region 38 to the front waist region 36 in a back-over-front manner. Alternatively, similar adhesive tape tabs may be attached to the chassis 100 in the front waist region 36 and used to fasten the front waist region 36 to the back waist region 38 in a front-over-back manner. Suitable adhesive tapes are available from the 3M Corporation of St. Paul, Minn., U.S.A., under the designation of XMF99121. Suitable configurations of adhesive tape tabs are disclosed in U.S. patent application Ser. No. 10/770,043 filed on 2 Feb. 2004.

When a laminate center sheet is used and is oriented with the nonwoven disposed exteriorly, some forms of mechanical fasteners that typically require specific mating fastener elements, such as hooks that mate with loops, may be configured to engage with the nonwoven and thereby make the inclusion of the specific mating fastener element unnecessary. Alternatively, when a nonwoven material is used to form the side flaps, a mechanical fastener such as the aforementioned hooks may be positioned on the exterior surface of the front waist region, such that when the back waist region of the diaper is brought into an overlapping configuration with the front waist region, the hook material engages the nonwoven material of the side flap.

Optionally, a fastening sheet 116 may be attached onto the exterior surface 104 of the chassis 100 in the front waist region 36 as shown in FIG. 21. The fastening sheet 116, shown in FIG. 21 lies entirely inside the edges of the diaper 20. Alternatively, two or more discrete fastening sheets may be attached onto the exterior surface of the chassis, instead of a single fastening sheet. For example, two laterally opposing fastening sheets may be attached in locations approximately corresponding to the left and right portions of the single fastening sheet 116. When a fastening sheet is provided, the adhesive tape tabs may be adhered to the fastening sheet to fasten the back waist region 38 and the front waist region 36 together. The fastening sheet may be formed of a material used elsewhere in the diaper, such as a film or a nonwoven. In embodiments in which the chassis is extensible, it is preferred that any fastening sheet also be extensible such that the fastening sheet will not restrict the extensibility of the portion of the chassis onto which it is attached. For example, an extensible nonwoven may be used for the fastening sheet.

The fastening sheet serves to distribute the tensile force transmitted by each of the adhesive tape tabs over an area of the center sheet 26 that is larger than the adhered area of the adhesive tape tab. In addition, when a single fastening sheet such as fastening sheet 116 in FIG. 21 is used, the fastening sheet may, itself, bear a portion of the tensile force between the laterally opposing adhesive tape tabs and thereby relieve a portion of the force exerted on the center sheet. Thus, the incorporation of such a fastening sheet may be desirable, for example, in order to make it possible to use a relatively inexpensive and relatively weak material for the center sheet 26. The fastening sheet may be formed of a material having greater strength than the center sheet. Such a stronger material may be more expensive per unit area than the center sheet, but the fastening sheet may be relatively smaller than the center sheet. Therefore, the total cost of a diaper having a fastening sheet may be less than the total cost of a diaper having a center sheet having sufficient strength for adhesive tape tabs to be adhered directly to the exterior surface of the center sheet.

As another example, cohesive fastening elements may be used. Exemplary fastening elements in the form of cohesive fastening patches, such as the patches 110 and 120 shown in FIG. 1, FIG. 2, FIG. 3, and FIG. 6 may be formed of an inherently crystalline water-based synthetic elastomer to which a tackifying agent has been added to disrupt the polycrystalline structure and thereby render the elastomer cohesive. Such synthetic cohesive products are available from Andover Coated Products, Incorporated, of Salisbury, Mass., U.S.A. and are described in U.S. Pat. No. 6,156,424 issued on 5 Dec. 2000 in the name of Taylor. Cohesive fastening patches may be disposed on the exterior and/or interior surfaces of the chassis in arrangements that allow exclusively for either back-over-front fastening or front-over-back fastening of the waist regions together. Alternatively, the cohesive fastening patches may be disposed in a reversible configuration that is adapted to provide the user of the diaper with both options for fastening, i.e., either back-over-front or front-over-back, in the same diaper, according to personal preference. Suitable configurations of cohesive fastening elements are disclosed in U.S. patent application Ser. No. 10/770,043 filed on 2 Feb. 2004.

Description of the Absorbent Assembly

Figure 22:
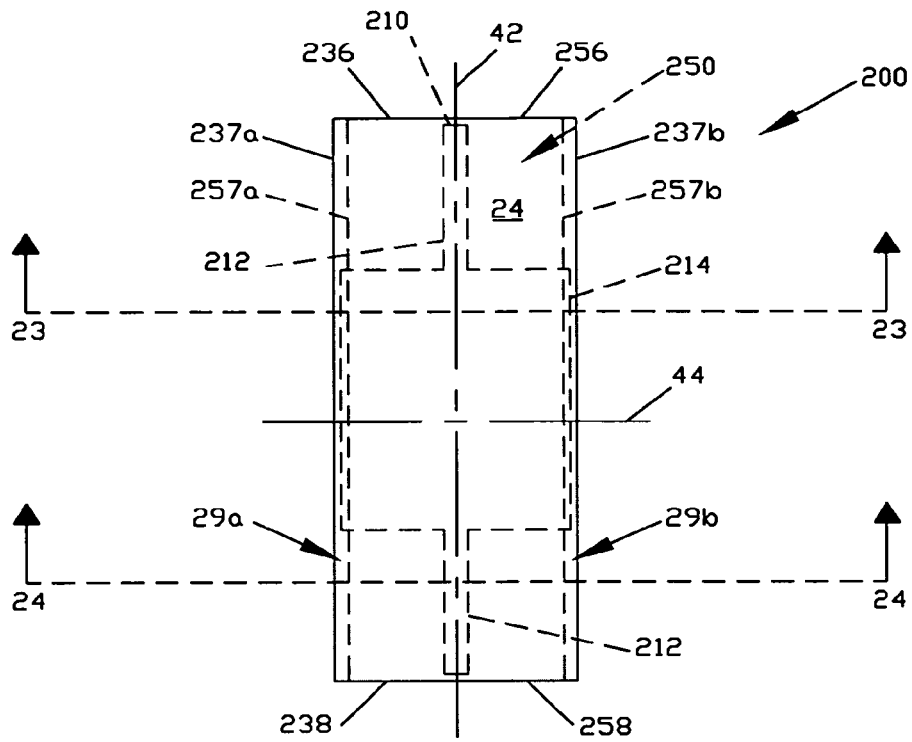
FIG. 22 is a plan view of an exemplary absorbent assembly 200.
Figure 23:
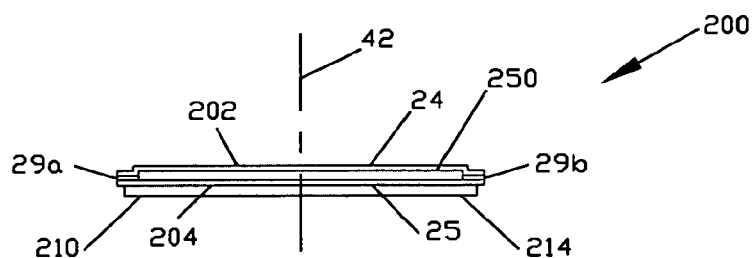
FIG. 23 is a section view of the absorbent assembly 200 of FIG. 22 taken at the section line 23-23.
Figure 24:
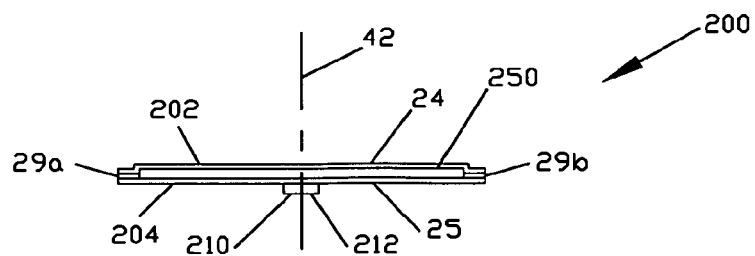
FIG. 24 is a section view of the absorbent assembly 200 of FIG. 22 taken at the section line 24-24.

As shown in FIG. 22, FIG. 23, and FIG. 24, the absorbent assembly 200 includes an absorbent core 250 that serves to absorb and retain liquid bodily waste materials. The absorbent core 250 has a laterally extending front edge 256 and a longitudinally opposing and laterally extending back edge 258. The absorbent core 250 also has a longitudinally extending left side edge 257a and a laterally opposing and longitudinally extending right side edge 257b, both absorbent core side edges extending longitudinally between the front edge 256 and the back edge 258. The absorbent core 250 also has an interior surface 252 and an exterior surface 254.

The absorbent assembly 200 may be attached to the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern.

An exemplary contiguous cruciform attachment pattern 210 is shown in FIG. 22, FIG. 23, and FIG. 24. The portions of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIG. 24 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 22 and FIG. 23 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness and positioning of the side flaps 147a and 147b when the elastic strands 167a and 167b lift the proximal edges 157a and 157b into contact with the body of the wearer. For example, if the absorbent assembly was attached only along the longitudinal centerline, the absorbent assembly could be compressed by the legs to a smaller lateral dimension than desired. This narrowing of the absorbent assembly would in turn allow the chassis 100 in the crotch region 37 to narrow, i.e., allow the left side edge 137a and/or the right side edge 137b to move toward the longitudinal axis 42. Such narrowing of the chassis 100 would increase the likelihood that the side flaps 147a and 147b would distort and fail to maintain contact with the body and/or become improperly positioned. However, because the relatively wide laterally extending portion 214 of the cruciform attachment pattern 210 restrains the chassis 100 over a relatively wide portion of the width of the crotch region 37, the side flaps 147 are more likely to remain properly positioned while being lifted by the elastic strands 167.

Within the extent of the cruciform attachment pattern 210, the absorbent assembly 200 may be attached to the chassis 100 continuously or intermittently. For example, a film of an adhesive may be applied continuously over the entire area of the cruciform attachment pattern and then used to continuously attach the absorbent assembly to the chassis. As an alternative example, an adhesive may be applied discontinuously at and inside the boundaries of the cruciform attachment pattern, such as in the form of dots, stripes, beads, spirals, etc., and then used to attach the absorbent assembly to the chassis.

The cruciform attachment pattern 210 may be disposed symmetrically with respect to either or both of the longitudinal axis 42 and the lateral axis 44 of the chassis 100. Alternatively, the cruciform attachment pattern 210 may be disposed asymmetrically with respect to either or both of the longitudinal axis 42 and the lateral axis 44. In addition, the cruciform attachment pattern 210 may be disposed symmetrically with respect to either or both of the side edges 237 and the front edge 236 and the back edge 238 of the absorbent assembly 200. Alternatively, the cruciform attachment pattern 210 may be disposed asymmetrically with respect to either or both of the side edges 237 and front edge 236 and back edge 238.

Suitable configurations of cruciform attachment patterns are disclosed in U.S. patent application Ser. No. 10/880,128 filed on 29 Jun. 2004.

The absorbent core 250 may be disposed between a lower covering sheet that is disposed on the exterior face of the absorbent core 250 and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in FIG. 22, FIG. 23, and FIG. 24, an upper covering sheet 24 and a lower covering sheet 25 are attached together at or adjacent to the side edges 237 of the absorbent assembly 200 in longitudinally extending adhesive attachment zones 29a and 29b. Alternatively, the upper covering sheet 24 and the lower covering sheet 25 may be attached together in places other than the side edges 237, e.g., at or adjacent to the end edges 236 and 238 of the absorbent assembly 200, or at or adjacent to both the end edges 236 and 238 and the side edges 237. Both the upper covering sheet and the lower covering sheet are water vapor-permeable, i.e., breathable.

The upper covering sheet 24 is water-permeable and allows liquid waste to pass through to the absorbent core 250, where the liquid waste is absorbed. The lower covering sheet 25 may be water-impermeable. However, the lower covering sheet 25 preferably is water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 may form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the center sheet 26.

The upper covering sheet 24 and the lower covering sheet 25 may extend to the same width and the same length. Alternatively, one or more of the edges of one of the covering sheets may lie distally relative to the respective edge or edges of the other covering sheet. For example, the upper covering sheet may extend longitudinally only to an extent sufficient to cover the absorbent core and the lower covering sheet may extend longitudinally beyond the upper covering sheet toward or to the adjacent waist edge. Such an extended covering sheet may serve to isolate the skin of the wearer from a portion of the center sheet 26 as may be desirable, for example, when the diaper 20 is worn under conditions in which contact between the skin and a center sheet film could be uncomfortable.

In the exemplary absorbent assembly 200 shown in FIG. 22, FIG. 23, and FIG. 24, the upper covering sheet 24 and the lower covering sheet 25 are of the same size, i.e., both the upper covering sheet 24 and the lower covering sheet 25 extend to the front edge 236 and back edge 238, as well as to both side edges 237 of the absorbent assembly 200. Alternatively, the upper covering sheet 24 and the lower covering sheet 25 may differ in size. For example, the lower covering sheet 25 may be larger than the upper covering sheet 24 and may be wrapped over the side edges 257 of the absorbent core 250 onto the interior surface of the absorbent core 250, where the upper covering sheet 24 and the lower covering sheet 25 may be attached together. Alternatively, in place of a separate upper covering sheet 24 and a separate lower covering sheet 25, a single covering sheet may be wrapped around the absorbent core 250 and attached to itself to contain the absorbent core 250. Such a single covering sheet forms an upper layer and a lower layer when wrapped around the absorbent core 250 and, in general, the description of the separate upper covering sheet 24 and lower covering sheet 25 are intended to apply to such upper and lower layers of a wrapped single covering sheet.

The absorbent core 250 includes a storage component that serves to absorb and retain liquid bodily waste materials. Suitable known materials for the absorbent core storage component include cellulose fibers in the form of comminuted wood pulp, commonly known as "airfelt", natural or synthetic fibrous materials, and superabsorbent polymers, used either singly or in mixtures and commonly formed into layers or sheets, etc. These absorbent materials may be used separately or in combination. Many known absorbent materials may be used in a discrete form, i.e., in the form of fibers, granules, particles, and the like. Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Figure 25:
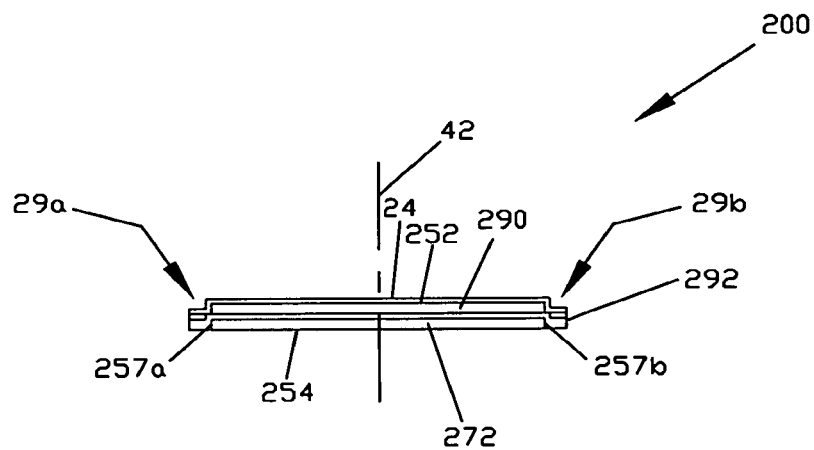
FIG. 25 is a section view of an exemplary absorbent assembly 200.

Such an absorbent core 250 including an acquisition component 290 overlying an absorbent core storage component 272 is shown in FIG. 25. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer. This separation sheet 292 may extend laterally beyond the side edges 257a and 257b of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 26:
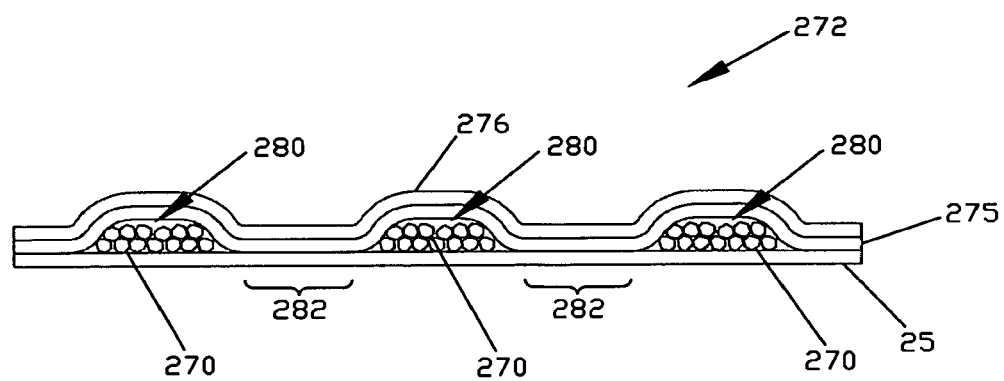
FIG. 26 is a section view of an exemplary absorbent assembly 200.

In some exemplary embodiments, an absorbent core storage component may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in U.S. patent application Ser. Nos. 10/776,839 and 10/776,851, both filed on 11 Feb. 2004 in the name of Ehrnsperger et al. An exemplary absorbent core storage component 272 having such a structure is shown in FIG. 26. In this absorbent core storage component 272, particles 270 of a superabsorbent polymer are contained inside pockets 280 formed by a layer 275 of a thermoplastic material. The absorbent core storage component may include both particles of superabsorbent polymer and airfelt and both materials may be contained inside the pockets formed by the layer of the thermoplastic material. Alternatively. as shown in FIG. 26, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 26, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid waste may pass to the particles to be absorbed by the particles 270 of the superabsorbent polymer.

In FIG. 26, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 26 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet and/or a separate upper covering sheet.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article, comprising:
   a. a water-permeable covering sheet;
   b. a water-impermeable center sheet comprising a first side edge, an opposing second side edge, a first side that faces toward the water-permeable covering sheet, and a second side that faces away from the water-permeable covering sheet;
   c. an absorbent core disposed between a water-permeable covering sheet and a water-impermeable center sheet;
   d. a pair of side flaps comprising a first side flap and an opposing second side flap; each of the first and second side flaps being made from a distinct layer of material that is not an extension of the water-permeable covering sheet or the water-impermeable center sheet;
   e. wherein the distinct layer of material is doubled over to form a first layer comprising a first layer proximal edge, and a second layer comprising a second layer proximal edge;
   f. wherein the first layer and the second layer enclose an elastic strand;
   g. wherein the first layer is attached to the second layer;
   h. wherein the first layer proximal edge of the first side flap is disposed laterally inward from the first side edge of the water-impermeable center sheet and is attached to the second side of the water-impermeable center sheet, but is disposed laterally outward from the second layer proximal edge of the first flap that is also attached to the second side of the water-impermeable center sheet and
   i. wherein the first layer proximal edge of the second side flap is disposed laterally inward from the second side edge of the water-impermeable center sheet and is attached to the second side of the water-impermeable center sheet, but is disposed laterally outward from the second layer proximal edge of the second flap that is also attached to the second side of the water-impermeable center sheet.

2. The disposable absorbent article of claim 1, wherein the absorbent core is asymmetric about a lateral axis of the article.

3. The disposable absorbent article of claim 1, wherein the absorbent core comprises an acquisition component overlying a storage component.

4. The disposable absorbent article of claim 1, wherein the absorbent core comprises wood pulp and superabsorbent polymer.

5. The disposable absorbent article of claim 1, wherein the side flaps are water vapor permeable.

6. The disposable absorbent article of claim 1, wherein the side flaps comprise a nonwoven.

7. The disposable absorbent article of claim 1, wherein the side flaps comprise a spunbond meltblown nonwoven.

8. The disposable absorbent article of claim 1, wherein the article has a chassis that is hourglass-shaped.

9. The disposable absorbent article of claim 1, wherein the water-impermeable center sheet comprises a polyolefin film.

10. The disposable absorbent article of claim 1, wherein the article is an incontinence article.

11. The disposable absorbent article of claim 10, wherein the incontinence article is a diaper.

* * * * *